United States Patent [19]
Hartman et al.

[11] Patent Number: 5,272,158
[45] Date of Patent: Dec. 21, 1993

[54] FIBRINOGEN RECEPTOR ANTAGONISTS

[75] Inventors: George D. Hartman, Lansdale; Melissa Egbertson, Ambler; Laura M. Turchi, Broomall; Laura A. Birchenough, Hatfield, all of Pa.

[73] Assignee: Merck & Co., Inc., Rahway, N.J.

[21] Appl. No.: 821,116

[22] Filed: Jan. 15, 1992

Related U.S. Application Data

[63] Continuation-in-part of Ser. No. 784,484, Oct. 29, 1991, abandoned.

[51] Int. Cl.$^5$ .................. C07D 401/06; A61K 31/445
[52] U.S. Cl. ...................................... 514/323; 546/201
[58] Field of Search .................... 546/201; 514/323

[56] References Cited

U.S. PATENT DOCUMENTS

| | | | |
|---|---|---|---|
| 4,122,255 | 10/1992 | Krapcho | 544/160 |
| 4,243,807 | 1/1981 | Friebe et al. | 546/232 |
| 4,622,331 | 11/1986 | Jozic | 514/331 |
| 5,030,654 | 7/1991 | Barnish | 514/510 |

FOREIGN PATENT DOCUMENTS

| | | |
|---|---|---|
| 0352249 | 1/1990 | European Pat. Off. |
| 0372486 | 6/1990 | European Pat. Off. |
| 0381033 | 8/1990 | European Pat. Off. |
| 0384362 | 8/1990 | European Pat. Off. |
| 0405537 | 1/1991 | European Pat. Off. |

*Primary Examiner*—C. Warren Ivy
*Assistant Examiner*—Phyllis G. Spivack
*Attorney, Agent, or Firm*—Richard S. Parr; Melvin Winokur

[57] ABSTRACT

Fibrinogen receptor antagonists of the formula:

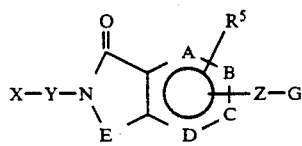

are disclosed for use in inhibiting the binding of fibrinogen to blood platelets and for inhibiting the aggregation of blood platelets wherein G is:

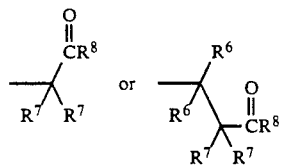

7 Claims, No Drawings

FIBRINOGEN RECEPTOR ANTAGONISTS

CROSS-REFERENCE TO RELATED APPLICATIONS

This application is a continuation-in-part patent application of U.S. Ser. No. 07/784,484, filed Oct. 29, 1991 now abandoned.

FIELD OF THE INVENTION

This invention relates to the discovery of fibrinogen receptor antagonists of Formula I for use in inhibiting the binding of fibrinogen to blood platelets and inhibiting the aggregation of blood platelets when administered to mammals, preferably humans.

BACKGROUND OF THE INVENTION

The interaction of platelets with the coagulation and fibrinolytic systems in the maintenance of hemostasis may become pathogenic, requiring prevention and treatment. The fibrinogen receptor antagonists of Formula I are useful in treating various diseases related to platelet aggregation and fibrin formation.

An interest in platelet inhibitors has reemerged as a result of a better understanding of the role of platelets and thrombosis in the pathogenesis of vascular disease, including unstable angina, acute myocardial infarction and stroke.

Platelets are cell-like anucleated fragments, found in the blood of all mammals which participate in blood coagulation. Fibrinogen is a glycoprotein present as a normal component of blood plasma. Fibrinogen participates in platelet aggregation and fibrin formation in the blood clotting mechanism. Platelets are deposited at sites of vascular injury where multiple physiological agonists act to initiate platelet aggregation culminating in the formation of a platelet plug to minimize blood loss. If the platelet plug occurs in the lumen of a blood vessel, normal blood flow is impaired.

Platelet membrane receptors are essential in the process of platelet adhesion and aggregation. Interaction of fibrinogen with a receptor on the platelet membrane complex IIb/IIIa is known to be essential for normal platelet function.

Zimmerman et al., U.S. Pat. No. 4,683,291, describes peptides having utility in the study of fibrinogen-platelet, platelet-platelet, and cell-cell interactions. The peptides are described as having utility where it is desirable to retard or prevent formation of a thrombus or clot in the blood. The general formula for the peptides is:

H$_2$N-(Ch)-Arg-Gly-Asp-(Cx)-H where Ch and Cx are sequences of amino acids.

Pierschbacher et al., U.S. Pat. No. 4,589,881, describes the sequence of an 11.5 kDal polypeptide fragment of fibronectin which embodies the cell-attachment-promoting activity of fibronectin. A specifically described fragment is:

H—Tyr—Ala—Val—Thr—Gly—Arg—Gly—Asp—
Ser—Pro—Ala—Ser—Ser—Lys—Pro—Ile—
Ser—Ile—Asn—Tyr—Arg—Thr—Glu—Ile—
Asp—Lys—Pro—Ser—Gln—Met—OH

Ruoslahti et al., U.S. Pat. No. 4,614,517, describes tetrapeptides which alter cell-attachment activity of cells to various substrates. The peptides are stated to "consist essentially of" the following sequence:

X-Arg-Gly-Asp-Ser-Y wherein X is H or one or more amino acids and Y is OH or one or more amino acids. FIG. 1 lists the polypeptides that were synthesized by Ruoslahti et al. in "determining the smallest peptide exhibiting cell attachment activity". Ruoslahti et al., U.S. Pat. No. 4,578,079, describes similar tetrapeptides having Ser substituted with Thr or Cys.

Pierschbacher et al., *Proc. Natl. Acad. Sci. USA*, Vol. 81, pp 5985–5988, October, 1984, describe variants of the cell recognition site of fibronectin that retain attachment-promoting activity. Pierschbacher et. al. further assayed the cell attachment-promoting activities of a number of structures closely resembling the Arg-Gly-Asp-Ser peptide, and found "that the arginine, glycine, and aspartate residues cannot be replaced even with closely related amino acids, but that several amino acids can replace serine without loss of activity."

Ruoslahti et al., *Science*, Vol. 238, pp. 491–497, Oct. 23, 1987, discuss cell adhesion proteins. They specifically state that "elucidation of the amino acid sequence of the cell-attachment domain in fibronectin and its duplication with synthetic peptides establish the sequence Arg-Gly-Asp (RGD) as the essential structure recognized by cells in fibronectin."

Cheresh. *Proc. Natl. Acad. Sci. USA*. Vol. 84, pp. 6471–6475, September 1987, describes the Arg-Gly-Asp-directed adhesion receptor involved in attachment to fibrinogen and the von Willebrand Factor.

Adams et al., U.S. Pat. No. 4,857,508, describes tetrapeptides which inhibit platelet aggregation and the formation of a thrombus. The tetrapeptides have the formula:

X-Gly-Asp-Y wherein X can be

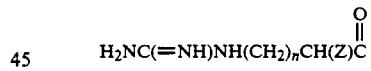

or Ac-Arg, wherein Z=H, NH$_2$, or NH-Acyl and n=1–4, and wherein Y can be Tyr-NH$_2$, Phe-NH$_2$ or a group of a specifically defined formula.

Tjoeng et al., EP 352,249, describe platelet aggregation inhibitors which antagonize interactions between fibrinogen and/or extracellular matrix proteins and the platelet gpIIb/IIIa receptor, including 8-guanido-octanoyl-Asp-2-(4-methoxyphenyl)ethyl amide.

Alig et al., EP 372,486, describe N-aryl beta-amino acids which inhibit fibrinogen, fibronectin and von Willebrand factor to the blood platelet fibrinogen receptor (glyco-protein IIb/IIIa).

Alig et al., EP 381,033, describe di-aryl or heteroaryl substituted alkanoic acid derivatives of a defined formula which inhibit binding of proteins to their specific receptors on cell surfaces, including fibrinogen.

Alig et al., EP 384,362, describe glycine peptides of a specified formula containing an amidine group which inhibit binding of fibrinogen to platelet fibrinogen receptors.

Horwell et al., EP 405,537, describe N-substituted cycloalkyl and polycycloalkyl alpha-substituted Trp- Phe- and phenethylamine derivatives which are useful for treating obesity, hypersecretion of gastric acid in the gut, gastrin-dependent tumors, or as antipsychotics.

It is an object of the present invention to provide fibrinogen receptor antagonists for use in inhibiting the binding of fibrinogen to blood platelets and inhibiting the aggregation of blood platelets. Another aspect of the present invention is to provide novel fibrinogen receptor antagonist compounds. Other objects of the present invention are to provide methods of inhibiting the binding of fibrinogen to blood platelets and inhibiting the aggregation of blood platelets, through the administration of novel fibrinogen receptor antagonist compounds. The above and other objects are accomplished by the present invention in the manner described below.

SUMMARY OF THE INVENTION

The present invention provides fibrinogen receptor antagonist compounds of the formula:

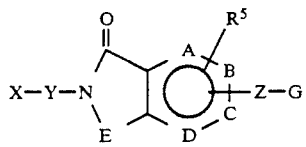

wherein G is

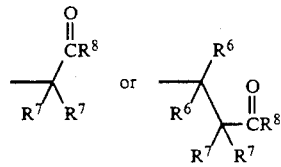

for use in inhibiting the binding of fibrinogen to blood platelets and for inhibiting the aggregation of blood platelets. The above-mentioned compounds can be used in a method of acting upon a fibrinogen receptor which comprises administering a therapeutically effective but non-toxic amount of such compound to a mammal, preferably a human. A pharmaceutical composition comprising a pharmaceutically acceptable carrier and, dispersed therein, an effective but non-toxic amount of such compound is another feature of this invention.

DETAILED DESCRIPTION OF THE INVENTION

Fibrinogen receptor antagonist compounds of Formula I are useful in a method of inhibiting the binding of fibrinogen to blood platelets and for inhibiting the aggregation of blood platelets. Fibrinogen receptor antagonists of this invention are illustrated by compounds having the formula:

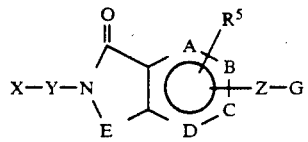

wherein G is

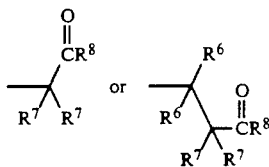

wherein:

A, B, C and D independently represent a carbon atom or a nitrogen atom;

E is $-(CHR^1)_m-(CHR^2)_n-Q-(CHR^3)_o-(CHR^4)_p-$; $-(CHR^1)_m-CR^2=CR^3-(CHR^4)_n-Q-$; or $-Q-(CHR^1)_m-CR^2=CR^3-(CHR^4)_n-$, wherein m, n, o, and p are integers chosen from 0-2., and Q is an optional substituent, which when present is chosen from:

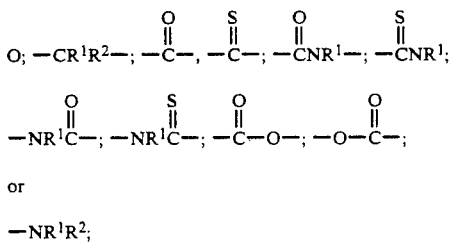

or $-NR^1R^2$;

X is

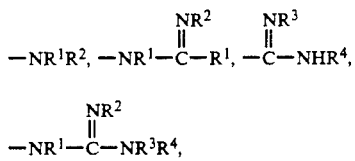

or a 4- to 10-membered mono- or polycyclic aromatic or non-aromatic ring system containing 0, 1, 2, 3 or 4 heteroatoms selected from N, O and S and either unsubstituted or substituted with $R^1$, $R^2$, $R^3$ or $R^4$, wherein $R^1$, $R^2$, $R^3$ and $R^4$ are independently selected from the group consisting of hydrogen, $C_1$ alkyl, aryl $C_{0-8}$ alkyl, oxo, thio, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy and hydroxy $C_{0-6}$ alkyl;

Y is $C_{0-8}$ alkyl, $C_{0-8}$ alkyl-$NR^3$-CO-$C_{0-8}$ alkyl, $C_{0-8}$ alkyl-CONR$^3$ $C_{0-8}$ alkyl. $C_{0-8}$ alkyl-O-$C_{0-8}$ alkyl, $C_{0-8}$ alkyl-S(O$_n$)-$C_{0-8}$ alkyl, or $C_{0-8}$ alkyl-SO$_2$-NR$^3$-$C_{0-8}$ alkyl-, $C_{0-8}$ alkyl-NR$^3$-SO$_2$-$C_{0-8}$ alkyl, $C_{1-8}$ alkyl-CO-$C_{0-8}$ alkyl;

Z is

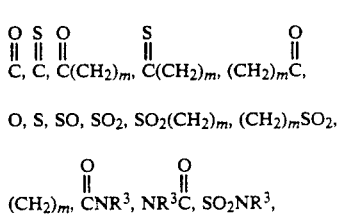

O, S, SO, SO$_2$, SO$_2$(CH$_2$)$_m$, (CH$_2$)$_m$SO$_2$, $(CH_2)_m$, $CNR^3$, $NR^3C$, $SO_2NR^3$,

-continued

wherein m is 0-6;

$R^5$ is hydrogen $C_{1-6}$ alkyl, $C_{0-6}$ alkylcarboxy $C_{0-6}$ alkyl, $C_{0-6}$ alkyloxy $C_{0-6}$ alkyl, hydroxy $C_{0-6}$ alkyl, aryl $C_{0-6}$ alkyl, or halogen;

$R^6$ is hydrogen, $C_{1-8}$ alkyl, aryl $C_{0-6}$ alkyl, $C_{3-8}$ cycloalkyl $C_{0-6}$ alkyl, $C_{0-6}$ alkylcarboxy $C_{0-6}$ alkyl, carboxy $C_{0-6}$ alkyl, $C_{1-4}$ alkyloxy $C_{0-6}$ alkyl, hydroxy $C_{0-6}$ alkyl, provided that any of which groups may be substituted or unsubstituted independently with $R^1$ or $R^2$, and provided that, when two $R^6$ groups are attached to the same carbon, they may be the same or different;

$R^7$ is hydrogen, fluorine $C_{1-8}$ alkyl, $C_{3-8}$ cycloalkyl, aryl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, aryl $C_{0-6}$ alkylsulfonylamino $C_{0-6}$ alkyl, $C_{1-8}$ alkyloxycarbonylamino $C_{0-8}$-alkyl, aryl $C_{0-8}$ alkyloxycarbonylamino $C_{0-8}$ alkyl, $C_{1-8}$ alkylcarbonylamino $C_{0-6}$ alkyl, aryl $C_{0-6}$ alkylcarbonylamino $C_{0-6}$ alkyl, $C_{0-8}$ alkylaminocarbonylamino $C_{0-6}$ alkyl, aryl $C_{0-8}$ alkylaminocarbonylamino $C_{0-6}$ alkyl, $C_{1-6}$ alkylsulfonyl $C_{0-6}$ alkyl, aryl $C_{0-6}$ alkylsulfonyl $C_{0-6}$ alkyl, $C_{1-6}$ alkylcarbonyl $C_{0-6}$ alkyl aryl $C_{0-6}$ alkylcarbonyl $C_{0-6}$ alkyl, $C_{1-6}$ alkylthiocarbonylamino $C_{0-6}$ alkyl aryl $C_{0-6}$ alkylthiocarbonylamino $C_{0-6}$ alkyl wherein groups may be unsubstituted or substituted with one or more substituents selected from $R^1$ and $R^2$, and provided that when two $R^7$ groups are attached to the same carbon atom, they may be the same or different;

$R^8$ is hydroxy. $C_{1-8}$ alkyl aryl $C_{0-6}$ alkyloxy, $C_{1-8}$ alkylcarbonyloxy $C_{1-4}$ alkyloxy, aryl $C_{1-8}$ alkylcarbonyloxy $C_{1-4}$ alkyloxy, or an L- or D-amino acid joined by an amide linkage and wherein the carboxylic acid moiety of said amino acid is as the free acid or is esterified by $C_{1-6}$ alkyl.

When substituent $R^1$, $R^2$, $R^3$, $R^4$, $R^5$, $R^6$, $R^7$, $R^8$ or Y includes the definition $C_0$, (e.g. aryl $C_0$ alkyl), the group modified by $C_0$ is not present in the substituent.

"Aryl" means a mono or polycyclic system composed of 5- and 6-membered aromatic rings containing 0, 1, 2, 3 or 4 heteroatoms chosen from N, O or S and either unsubstituted or substituted with $R^1$.

"Alkyl" means straight or branched chain alkane, alkene or alkyne.

"Halogen" includes fluorine, chlorine, iodine and bromine.

"Oxo" means =O.

"Thio" means =S. A preferred embodiment of the present invention is

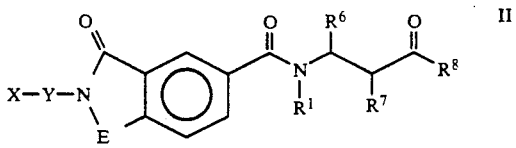

II wherein:

E is: $-(CHR^1)_m-(CHR^2)_n-Q-(CHR^3)_o-(CHR^4)_p-$, $-(CHR^1)_m-CR^2=CR^3-(CHR^4)_n-Q-$, or $-Q-(CHR^1)_m-CR^2=CR^3-(CHR^4)_n-$, where m, n, o and p are integers 0-2.

Q is an optional substituent which when present is chosen from:

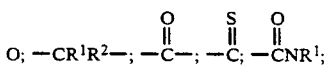

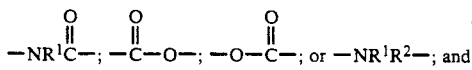

X, Y, $R^1$, $R^2$, $R^3$, $R^4$, $R^6$, $R^7$ and $R^8$ are as previously defined.

A more preferred embodiment of the present invention is III wherein:

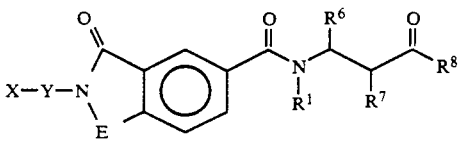

E is: $-(CHR^1)_m-Q-(CHR^2)_n-$, $-CR^1=CR^2-Q-$, or $-Q-CR^1=CR^2-$, where m and n are integers 0-2 and Q is an optional substituent which when present is chosen from:

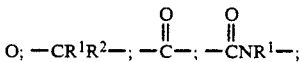

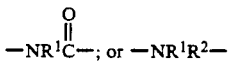

X is $-NR^1R^2$ or a 4- to 10-membered mono- or polycyclic aromatic or non-aromatic ring system containing 0, 1 or 2 heteroatoms chosen from N or O and either unsubstituted or substituted with $R^1$ and $R^2$, wherein $R^1$ and $R^2$ are independently chosen from: hydrogen, $C_{1-6}$ alkyl, aryl $C_{0-6}$ alkyl, carboxy $C_{0-6}$ alkyl, hydroxy $C_{0-6}$ alkyl, $C_{1-3}$ alkyloxy $C_{0-6}$ alkyl, or amino $C_{0-6}$ alkyl:

Y is $C_{0-6}$ alkyl, $C_{1-6}$ alkyl-CO-$C_{0-6}$ alkyl, or $C_{0-6}$ alkyl-$NR^3$-CO-$C_{0-6}$ alkyl;

$R^6$ and $R^7$ are as previously defined and $R^8$ is hydroxy, $C_{1-4}$ alkyl, $C_{1-6}$ alkyloxy, aryl $C_{1-4}$ alkyloxy, or $C_{1-6}$ alkylcarbonyloxy $C_{1-4}$ alkyloxy.

Preferred compounds of the invention are:

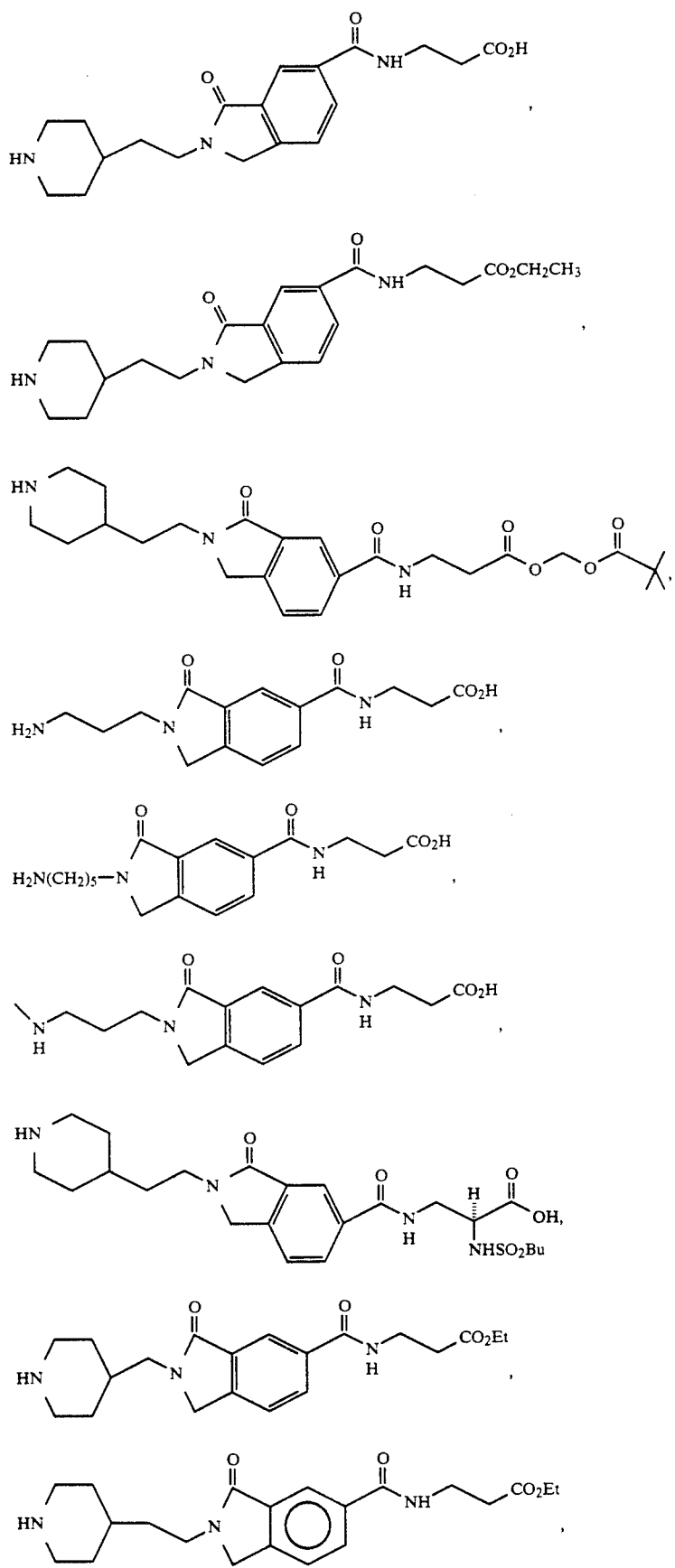

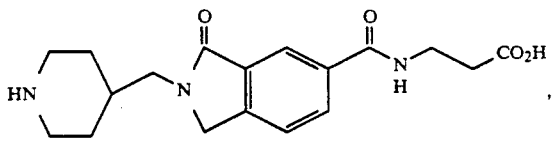

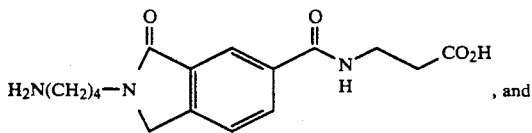
, and

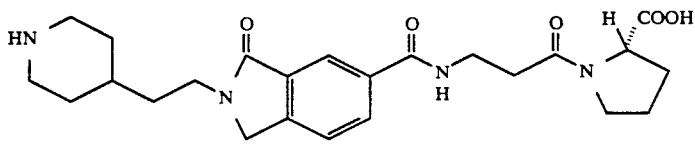

Generally, compounds of the present invention can be made according to a procedure including the following steps:

a) preparing a triflate activated aromatic group of the following general formula:

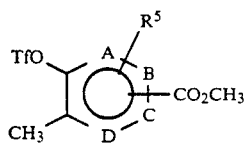

using

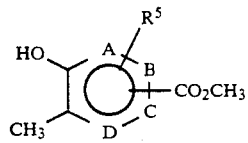

and Tf$_2$O;

b) inserting a carbonyl group for the triflate group using metal catalyzed carbonyl insertion, followed by trapping with methanol, to form

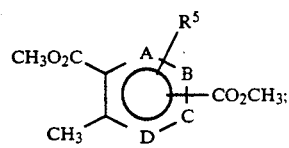

c) brominating the heterocyclic methyl group to form

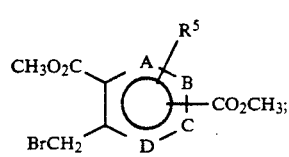

d) cyclizing with a primary amine to form

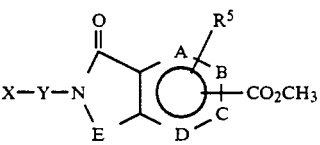

wherein X is an N-terminus protected primary amine, or a primary amine protected directly following this cyclization step;

e) converting the C-terminus ester, via hydrolysis, to an acid

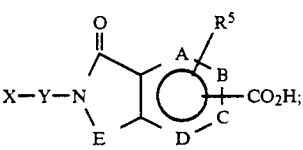

f) coupling the acid with an unsubstituted or substituted amino acid or C-terminus protected analog, or diamino acid or C-terminus protected analog, and optionally functionalizing the amino acid at the alpha- or beta-position, to form

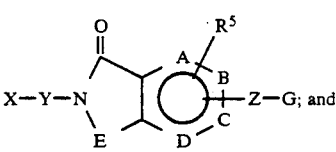

g) deprotecting the protected C-terminus and N-terminus.

Preferably the procedure involves
a) preparing an activated aryl group:

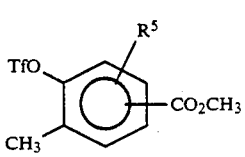

using

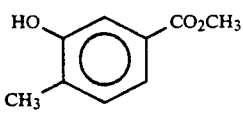

and T₂O;

b) inserting a carbonyl group for the triflate group using metal catalyzed carbonyl insertion followed by trapping with methanol to form

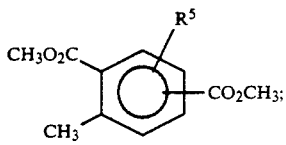

c) brominating the aryl methyl group to form

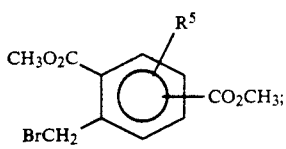

d) cyclizing with a primary amine to form

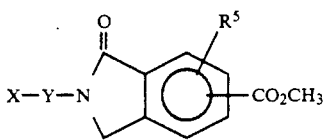

wherein X is an N-terminus protected primary amine, or a primary amine protected directly following this cyclization step;

e) converting the C-terminus ester, via hydrolysis to an acid

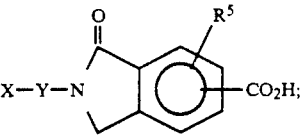

f) coupling the acid with an unsubstituted or substituted amino acid or C-terminus protected analog, or diamino acid or C-terminus protected analog, and optionally functionalizing the amino acid at the alpha- or beta-position via acylation or sulfonylation, to form

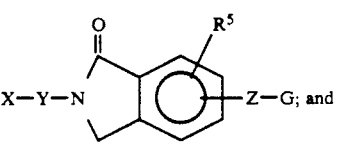

g) deprotecting the protected C-terminus and N-terminus.

An ADP-stimulated platelet aggregation assay was used to determine inhibition associated with compounds of the invention.

Human platelets were isolated from fresh blood, collected into acid citrate/dextrose by differential centrifugation followed by gel filtration on Sepharose 2B in divalent ion-free Tyrode's buffer (pH 7.4) containing 2% bovine serum albumin. Platelet aggregation was measured at 37° C. in a a Chronolog aggregometer. The reaction mixture contained gel-filtered human platelets ($2 \times 10^8$ per ml), fibrinogen (100 μg/ml), $Ca^{2+}$ (1 mM), and the compound to be tested. Aggregation was initiated by adding 10 uM ADP 1 minute after the other components had been added. The reaction was allowed to proceed for at least 2 minutes. The extent of inhibition of aggregation was expressed as the percentage of the rate of aggregation observed in the absence of inhibitor. The $IC_{50}$ is the dose of a particular compound inhibiting aggregation by 50% relative to a control lacking the compound.

Additional preferred embodiments of the invention, shown below with platelet aggregation inhibition potency date ($IC_{50}$ μM), are shown below.

-continued

| Compound | IC$_{50}$ uM |
|---|---|
| 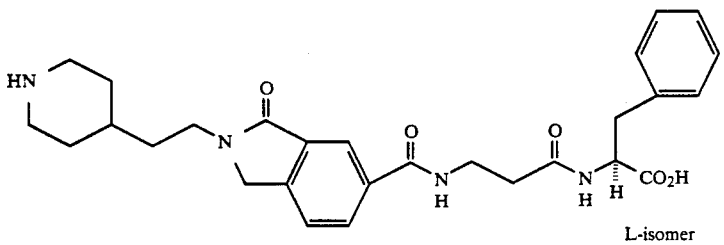 | 0.42 |
| L-isomer | |
| 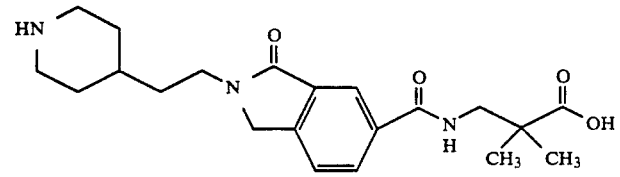 | 1.0 |
| 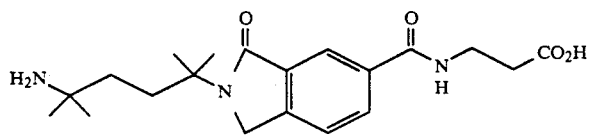 | 21 |
| 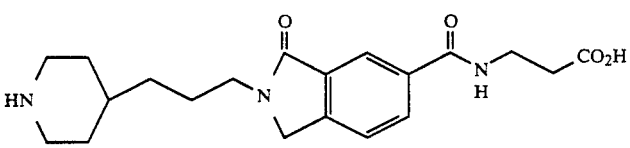 | 0.92 |
| 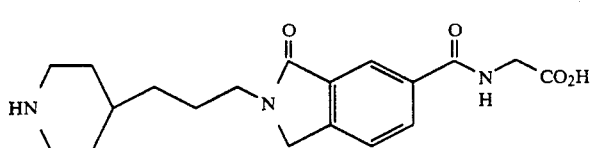 | 14.0 |

The abbreviations listed below are defined as Bn, benzyl; NMM, N-methylmorpholine: HOBt, 1-hydroxybenzotriazole; EDC, 1-(3-dimethylaminopropyl)-3-ethylcarbodiimide hydrochloride; DMF, dimethylformamide; Pib, 4-(4-piperidyl)butanoyl; pTSA, para-toluenesulfonic acid; DMS, dimethylsulfide; TFA, trifluoroacetic acid; THF, tetrahydrofuran; DIBAL, diisobutylaluminum hydride; Boc (or BOC), tert butoxycarbonyl; Cbz, benzyloxycarbonyl; Suc, succinoyl; alpine borane, β-isopinocamphenyl-9-borabicyclo[3.3.1]-nonane; TBDMS, tert-butyldimethylsilyl; Jones reagent, chromic acid; NBS, N-Bromosuccinimide; BPO, Benzoyl peroxide; PPh$_3$, triphenyl phosphine; DMSO, Dimethylsulfoxide; Et$_3$N, triethylamine; Tf$_2$O, triflic anhydride; DMAP, 4-dimethylaminopyridine; BOP, benzotriazol-1-yloxytris(dimethylamino)-phosphonium hexafluorophosphate; PhCHO, benzaldehyde; and Boc$_2$O, di-t-butyldicarbonate; dppp, 1,3-bis(-diphenylphosphino)propane; ETOH, ethyl acetate; CH$_2$Cl$_2$, methylene chloride; HOAc, acetic acid; CH$_{30}$H, methanol; CHCl$_3$, chloroform.

Unless otherwise indicated, all degree values are Celsius.

The pharmaceutically acceptable salts of the compounds of Formula I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of Formula I are useful in inhibiting the binding of fibrinogen to blood platelets, inhibiting aggregation of blood platelets, treatment of thrombus formation or embolus formation, and in the prevention of thrombus formation or embolus formation. These compounds are useful as pharmaceutical agents for mammals, especially for humans. The compounds of this invention may be administered to patients where prevention of thrombosis by inhibiting binding of fibrinogen to the platelet membrane glycoprotein complex IIb/IIIa receptor is desired. Compounds of this invention may also be used to prevent or modulate the progress of myocardial infarction, unstable angina and thrombotic stroke, in either acute or chronic settings. In addition, they may be useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. (Gluszko et al., Amer. J. Physiol. 1987, 252:H, pp 615–621). Platelets released from artificial surfaces show impaired hemostatic function. Compounds of this invention may be administered to prevent adhesion.

Other applications of these compounds include prevention of platelet thrombosis, thromboembolism, reocclusion, and restenosis during and after thrombolytic therapy and prevention of platelet thrombosis, thromboembolism, reocclusion and restenosis after angioplasty of coronary and other arteries and after coronary artery bypass procedures.

The compounds of Formula I may be administered to mammals, preferably in combination with pharmaceutically-acceptable carriers or diluents, optionally with known adjuvants such as alum, in a pharmaceutical composition which is non-toxic and in a therapeutically effective amount, according to standard pharmaceutical practice. The compounds can be administered orally or parenterally, including intravenous, intramuscular, intraperitoneal, trans-dermal, subcutaneous and topical administration.

For oral use of a fibrinogen receptor antagonist according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added.

For intramuscular, intraperitoneal, subcutaneous, and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment and prevention of diseases related to platelet aggregation, fibrin formation, and thrombus and embolus formation, comprising the administration of a therapeutically effective but non toxic amount of the compounds of Formula I, with or without pharmaceutically acceptable carriers or diluents.

Compositions of this invention include fibrinogen receptor antagonist compounds of this invention in combination with pharmacologically acceptable carriers, e.g. saline, at a pH level e.g. 7.4, suitable for achieving inhibition of platelet aggregation. The compositions may also be combined with anticoagulants such as heparin or warfarin. The compositions may also be combined with thrombolytic agents such as plasminogen activators or streptokinase in order to inhibit platelet aggregation in more acute settings. The composition may further be combined with antiplatelet agents such as aspirin. The compositions are soluble in an aqueous medium, and may therefore be effectively administered in solution.

When a compound according to Formula I is used as a fibrinogen receptor antagonist in a human subject, the daily dosage will normally be determined by the prescribing physician with the dosage generally varying according to the age, weight, and response of the individual patient, as well as the severity of the patients symptoms.

In one exemplary application, a suitable amount of compound is administered orally to a heart attack victim subsequent to angioplasty. Administration o:curs subsequent to angioplasty, and is in an amount sufficient to inhibit platelet aggregation, e.g. an amount which achieves a steady state plasma concentration of between about 0.01–50 $\mu$M preferably between about 0.01–10 $\mu$M.

The present invention also includes a pharmaceutical composition comprising compounds of the present invention in combination with tissue type plasminogen activator or streptokinase. The invention also includes a method for promoting thrombolysis and preventing reocclusion in a patient which comprises administering to the patient an effective amount of compositions of the invention.

The present invention provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non toxic amount of the compounds of this invention, with or without pharmaceutically acceptable carriers or diluents.

The present invention still further provides a method of inhibiting the binding of fibrinogen to blood platelets, inhibiting aggregation of blood platelets, treating thrombus formation or embolus formation, and in preventing thrombus formation or embolus formation in a mammal, comprising the administration of a therapeutically effective but non-toxic amounts of the compounds of this invention in combination with thrombolytic agents, such as tissue plasminogen activators or streptokinase, anticoagulants such as heparin or warfarin, or antiplatelet agents such as aspirin, with or without pharmaceutically acceptable carriers or diluents.

The compounds of Formula I are prepared according to the reaction schemes set forth below.
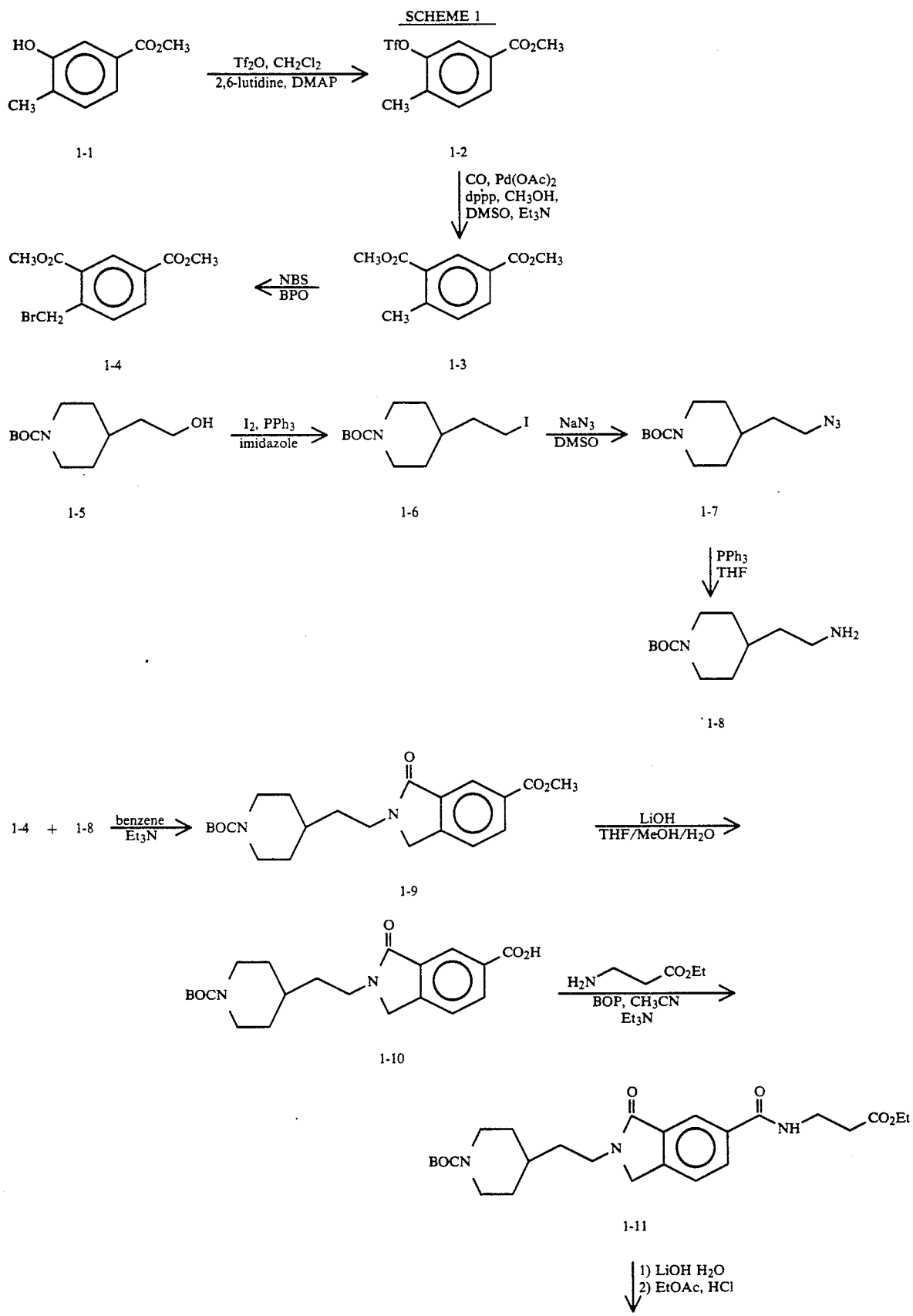
SCHEME 1

-continued
SCHEME 1

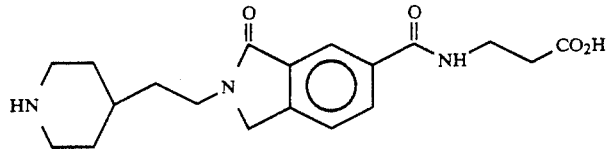

1-12

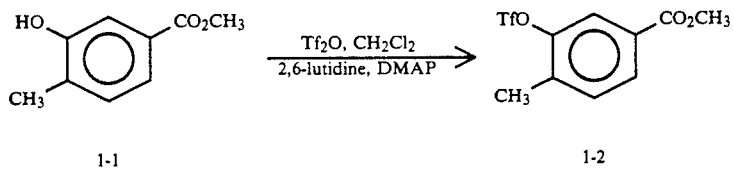

Methyl 4-methyl-3-trifluoromethanesulfonyloxy benzoate (1-2)

A solution of methyl 4-methyl-3-hydroxybenzoate (1-1) (20.0 g, 0.12 moles) [prepared from the corresponding carboxylic acid (Aldrich) by treatment with a methanolic solution of HCl gas] in CH$_2$Cl$_2$ (900 ml) was cooled to −40° and treated successively with 2,6-lutidine (0.18 moles), DMAP (2.9 g, 0.024 moles) and trifluoromethylsulfonyl anhydride (0.18 moles). The cooling bath was then removed and the resulting mixture was stirred at ambient temperature for 2.0 hours. The solvent was then removed and the residue was purified by flask chromatography on silica eluting with hexane(8-)/EtOAc(2) to provide pure 1-2, R$_f$ 0.35. $^1$H NMR (300 MHz, CDCl$_3$) δ 2.18 (3H, s), 3.85 (3H, s), 7.30 (1H, d), 7.84 (1H, s), 7.90 (1H, d).

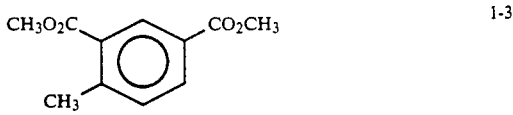

Dimethyl 4-methylbenzene-1,3-dicarboxylate (1-3)

A solution of 1-2 (30.0 g, 0.121 moles) in methanol/300 ml was treated successively with DMSO (180 ml), triethylamine (0.278 moles), palladium acetate (0.807 g, 3.6 mmoles) and dppp (1.48 g, 3.6 mmoles) as the reaction turned to a clear dark brown solution. Carbon monoxide was then bubbled through the reaction mixture for 3 minutes and the resulting mixture was heated at reflux, while continuing to bubble CO. After refluxing for 4 hours the reaction mixture was concentrated and the resulting brown oil was purified by flask chromatography on silica gel eluting with hexane(90-)/EtOAc(10) to provide pure 1-3.

$^1$H NMR (300 MHz, CDCl$_3$) δ 2.69 (3H, s). 3.95 (3H, s), 3.96 (3H, s), 7.37 (1H, d), 8.09 (1H, dd), 8.60 (1H, d).

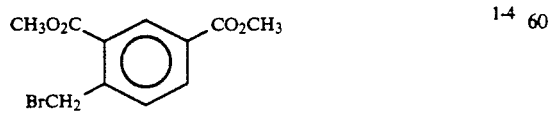

Dimethyl 4-bromomethylbenzene-1,3-dicarboxylic acid (1-4)

A solution of 1-3 (1.35 g, 6.5 mmole) in CHCl$_3$ (20 ml) was treated with dibenzoyl peroxide (0.078 g, 3.5 mmol) and N-bromosuccinimide (NBS) (1.1 g, 6.5 mmole) and the resulting solution was heated at reflux for 2 hours.

The cooled reaction mixture was concentrated, taken up in CCl$_4$, filtered and the filtrate was concentrated to give 1-4 as a tan solid. R$_f$ 0.5 [silica gel, hexane(70-)/EtOAc(30)].

Preparation of Boc-4-piperidine-2-ethanol (1-5)

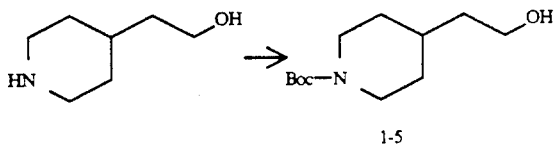

4-Piperidine-2-ethanol (Aldrich) (130 g, 1.0 mole) was dissolved in 700 mL dioxane, cooled to 0° C. and treated with 3N NaOH (336 mL, 1.0 mole), and di-t-butyldicarbonate (221.8 g, 1.0 mole). The ice bath was removed and the reaction stirred overnight. The reaction was concentrated, diluted with water and extracted with ether. The ether layers were combined, washed with brine, dried over MgSO$_4$, filtered and evaporated to give 1-5. R$_f$=0.37 in 1:1 EtOAc/Hexanes, ninhydrin stain.

$^1$H NMR (300MHz, CDCl$_3$) δ 4.07 (bs, 2H), 3.7 (bs, 2H), 2.7 (t, J=12.5 Hz, 2H), 1.8–1.6 (m, 6H), 1.51 (s, 9H), 1.1 (ddd, J=4.3, 12.5, 12 Hz, 2H).

Boc-4-piperidine-2-ethyl iodide (1-6)

Boc-4-piperidine-2-ethanol (1-5) (10.42 g, 0.048 mole was dissolved in 400 ml benzene and imidazole (4.66 g, 0.068 moles) and triphenylphosphine (15.24 g, 0.05 moles) were added at room temperature. After 6 hours the reaction mixture was filtered and the filtrate was evaporated to give a dark residue. This was purified by flash chromatography on silica gel eluting with 10% EtOAc-hexanes to give 1-6 as a yellow oil.

Boc-4-piperidine-2-ethylazide (1-7)

To 1-6 (27.9 g, 0.082 moles) dissolved in DMSO (400 ml) was added sodium azide (5.01 g, 0.086 moles) at room temperature and the resulting solution was heated at 65° for 2 hours. The cooled reaction mixture was diluted with 250 ml EtOAc, extracted with 2×100 ml portions of water 2×50 ml portions of brine and then dried (MgSO4) Solvent removal provided 1-7 as a pale yellow oil, R$_f$ 0.5 (silica gel. 70% acetone/hexane).

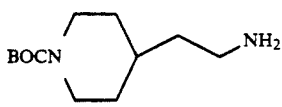

Boc-4-piperidine-2-ethylamine(1-8)

To a solution of 1-5 (19.3 g, 0.076 moles) in THF (400 ml)/H2O (195 ml) was added triphenylphosphine (80.0 g, 0.305 moles) in one portion at room temperature. This was stirred at room temperature 3 hours and the organic solvents were then removed in vacuo. The residue was acidified to pH 2 with 10% KHSO4 solution and this was extracted 4×100 ml portions of EtOAc. The organic extract was extracted with 2×100 ml portions of 10% KHSO4 and the aqueous phases were combined and the pH was adjusted to 10 with 2N NaOH. This solution was extracted with 4×200 ml portions of CH2Cl2. These were combined, dried (MgSO4) and the solvent was removed to give 1-8 as an oil. R$_f$ 0.3 (silica gel, eluting with 10% CH3OH in CHCl3/NH3)

$^1$H NMR (300 MHz, CDCl3) δ 4.05 (broad, 2H), 2.72 (t, J=7.2Hz, 2H), 2.62 (m, 2H), 1.64 (d, J=12.2Hz, 2H), 1.43 (s, 9H), 1.42–1.32 (m, 5H), 1.09 (m, 2H).

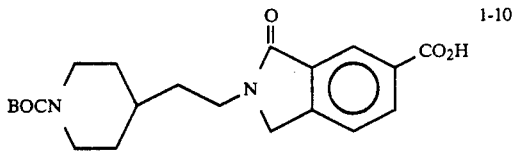

1-H-Isoindole-5-carboxylic acid, 2,3-dihydro-N-[2-(4-N-t-butyloxycarbonylpiperidinyl)ethyl]-3-oxo (1-10)

A solution of 1-9 (0.43 g, 1.12 mmole) in THF (1)/MeOH(1)/H2O (1) (9 ml) was treated at room temperature with LiOH.H2O (0.235 g, 5.6 mmol) and the resulting solution was stirred for 4 hours. The reaction mixture was then diluted with EtOAc (75 ml)/10% KHSO4 solution (30 ml) and the organic phase was separated and dried (Na2SO4) Solvent removal gave the desired acid 1-10 R$_f$ 0.5 (silica gel, CH2Cl2(9)/MeOH (0.5)/HOAc(0.5)).

$^1$H NMR (300 MHz, CDCl3) δ 1.12 (2H, m), 1.42 (9H, s), 1.60 (3H, m), 1.71 (2H, bd), 2.63 (2H, bt), 3.68 (2H, t), 4.08 (2H, m), 4.40 (2H, s), 7.03 (1H, d), 8.28 (1H, dd), 8.60 (1H, s).

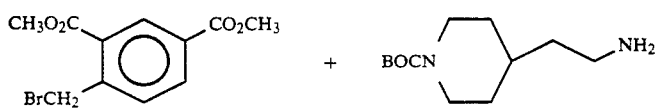

1-4                                1-8 benzene
Et3N

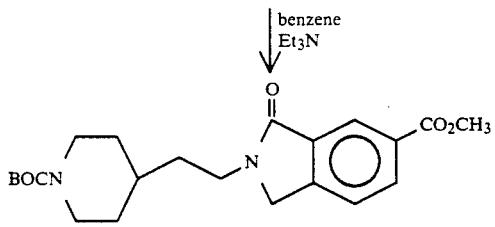

1-9

Methyl-1H-Isoindole-5-carboxylate, 2,3-dihydro-N-[2(4-N-t-butyloxycarbonylpiperidinyl)ethyl]-3-oxo (1-9)

A solution of 1-4 (1.0 g, 3.5 mmoles) in benzene (5 ml) was treated with 1-8 (0.80 g, 3.5 mmol) and triethylamine (0.49 ml, 3.5 mmol) and the reaction mixture was heated at reflux for 3 hours. The solvent was removed and the residue was taken up in EtOAc, washed in 10% KHSO4 solution, H2O, brine and dried. Solvent removal gave a residue that was purified by flash chromatography on silica gel eluting with hexane(1)/EtOAc(1) to give pure 1-9. R$_f$ 0.2 (silica gel, hexane(1)/EtOAc(1)).

$^1$H NMR (300 MHz, CDCl3) δ 1.08 (2H, m), 1.43 (9H, s) 1.61 (4H, m), 1.73 (2H, bd), 2.62 (2H, bt), 3.64 (2H, t), 3.93 (3H, s), 4.07 (2H, m), 4.40 (2H, s), 7.50 (1H, d), 8.21 (1H, dd), 8.47 (1H, d).

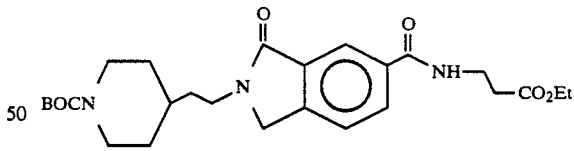

1-11

1-H-Isoindole-5-carboxamide, 2,3-dihydro-N-[2-(carboethoxy)ethyl]-2-[2-(4-N-t-butyloxycarbonylpiperidinyl)ethyl]-3-oxo (1-11)

A solution of 1-10 (0.35 g, 0.94 mmole), triethylamine (0.40 ml, 2.82 mmol), and B alanine ethyl ester (0.22 g, 1.41 mmol) (Aldrich) in CH3CN (5 ml) was treated at room temperature with BOP (1.2 mmoles) reagent and the resulting solution was stirred for 16 hours.

The solvent was removed and the residue was taken up in EtOAc, washed with H2O, 10% KHSO4 solution, brine and dried (Na2SO4) Solvent removal gave a residue that was purified by flash chromatography on silica gel eluting with hexane(20)/EtOAc(80) to give pure 1-11 as a clear oil.

$^1$H NMR (300 MHz. CDCl3) δ 1.10–1.30 (3H, m), 1.44 (9H, s), 1.60 (3H, m), 1.75 (2H, bd), 2.63 (4H, m), 3.70 (4H, m), 4.05–4.20 (4H, m), 4.38 (2H, s), 7.50 (1H, d), 8.08 (2H, m).

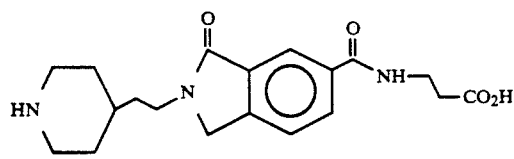

1-12

1-H-Isoindole-5-carboxamide, 2,3-dihydro-N-(2-carboxyethyl)-2-[2-(4-piperidinyl)ethyl]-3-oxo (1-12)

A solution of 1-11 (0.32 g, 0.68 mmol) in THF(1)/MeOH(1)/H₂O(1) (9 ml) was treated with LiOH.H₂O (0.14 g, 3.4 mmoles) at room temperature for 1.0 hr. The solvent was then removed and the residue was taken up in EtOAc and washed with 10% KHSO₄ solution, brine and dried (Na₂SO₄). Solvent removal gave the desired acid. R$_f$ 0.3 (silica gel, CHCl₃ (9)/MeOH (0.5)/HOAc (0.5)).

This acid (0.30 g, 0.68 mmole) was dissolved in CH₂Cl₂ and anisole (150 μl) was added. This was cooled to −15° C. and trifluoroacetic acid (3 ml) was added and the resulting mix stirred for 0.5 hours. The solvent was removed and the residue purified by flash chromatography on silica gel eluting with EtOH (9)/NH₄OH (1.2)/H₂O (1.2) to provide pure 1-12.

¹H NMR (300 MH₃, D₂O) δ 1.30 (7H, m), 1.50–1.70 (3H, m), 1.83 (2H, bd), 2.38 (2H, t), 2.80 (2H, dt), 3.27 (2H, bd), 3.50 (4H, m), 4.42 (2H, s), 7.51 (1H, d), 7.83 (2H, m).

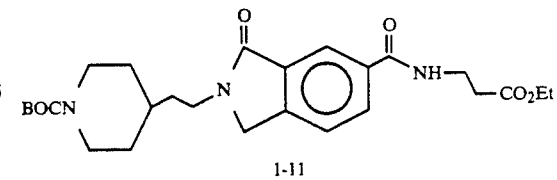

1-H-Isoindole-5-carboxamide, 2,3-dihydro-N-[2-(carboethoxy)ethyl]-2-[2-(4-piperidinyl)ethyl]-3-oxo (1-13)

A solution of 1-11 (0.72 g, 1.57 mmoles) in EtOAc (20 ml) was cooled to −78° C. and HCl gas was bubbled through. This solution for 1-2 minutes and the reaction mixture was then stirred at 0° C. After a few minutes a white solid had precipitated and this mixture was stirred for 0.5 hours. The solvent was then removed and the residue was triturated with Et₂O to give pure 1-13.

¹H NMR (300 MHz, CD₃OD) δ 1.23 (3H, t), 1.45 (2H, m), 1.66 (2H, m), 1.72 (2H, m), 2.07 (2H, m), 2.65 (2H, t), 2.94 (2H, m), 3.47 (2H, bd), 3.68 (4H, m), 4.12 (2H, q), 4.57 (2H, s), 7.67 (1H, d), 8.03 (1H, dd), 8.14 (1H, d).

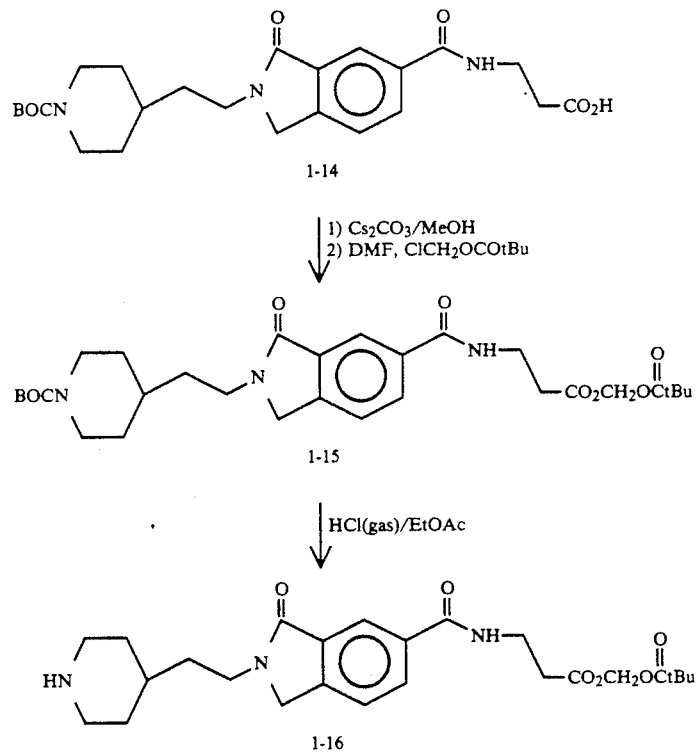

1H-Isoindole-5-carboxamide, 2,3-dihydro-N-[2-(t-butylcarbonyloxymethylcarboxy)ethyl]-2-[2-(4-N-t-butyloxycarbonylpiperidinyl)ethyl]-3-oxo (1-15)

A slurry of 1-16 (0.80 g, 1.8 mmoles) in MeOH (20 ml) was treated with $Cs_2CO_3$ (0.24 g, 0.90 mmoles) at room temperature and the resulting mixture was stirred for 45 minutes. The solvent was then removed and the residue was slurried in DMF (20 ml) and this was treated at room temperature with chloromethyl pivalate (1.8 mmoles). The resulting mixture was stirred at room temperature for 24 hours.

The reaction mixture was then diluted with EtOAc and washed with $H_2O$, 10% $KHSO_4$, saturated with $NaHCO_3$ solvent and brine. The organic phase was dried ($MgSO_4$), and the solvent removed to provide 1-15 as a white solid.

$^1$H NMR (300 MHz, $CDCl_3$) δ 1.11–1.25 (13H, m), 1.46 (9H, s), 1.63 (2H, q), 1.77 (2H, bd), 2.62–2.76 (4H. m). 3.72 (9H, m). 4.09 (2H, bd). 4.42 (2H, s), 5.80 (2H, s), 6.89 (1H, bt), 7.53 (1H, d), 8.09 (1H, d), 8.14 (1H. s).

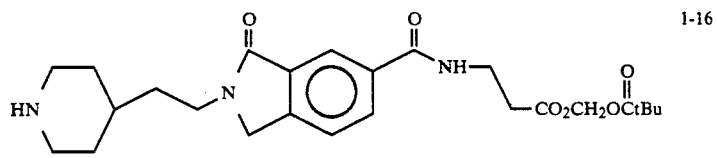

1-16

1-H-Isoindole-5-carboxamide, 2,3-dihydro-N-[2-(t-butylcarbonyloxymethylcarboxy)ethyl]-2-[2-(4-piperidinyl)ethyl]-3oxo -(1-16)

A solution of 1-15 (15 mg) in EtOAc (5 ml) was cooled to −78° C. and treated with HCl gas for 10 minutes and the resulting solution was stirred at −10° C. for 1.0 hour. The solvent was then removed to provide pure 1-16 as a white solid.

$^1$H NMR (300 MHz, $CD_3OD$) δ 1.06 (9H, s), 1.92 (1H, m), 1.70 (2H, m), 2.08 (2H, bd), 3.73 (2H, t), 2.95 (2H, dt), 3.38 (2H, bd), 3.70 (6H, m), 4.58 (2H, s), 5.86 (2H, s), 7.67 (1H, d), 8.06 (1H, d), 8.17 (1H, s).

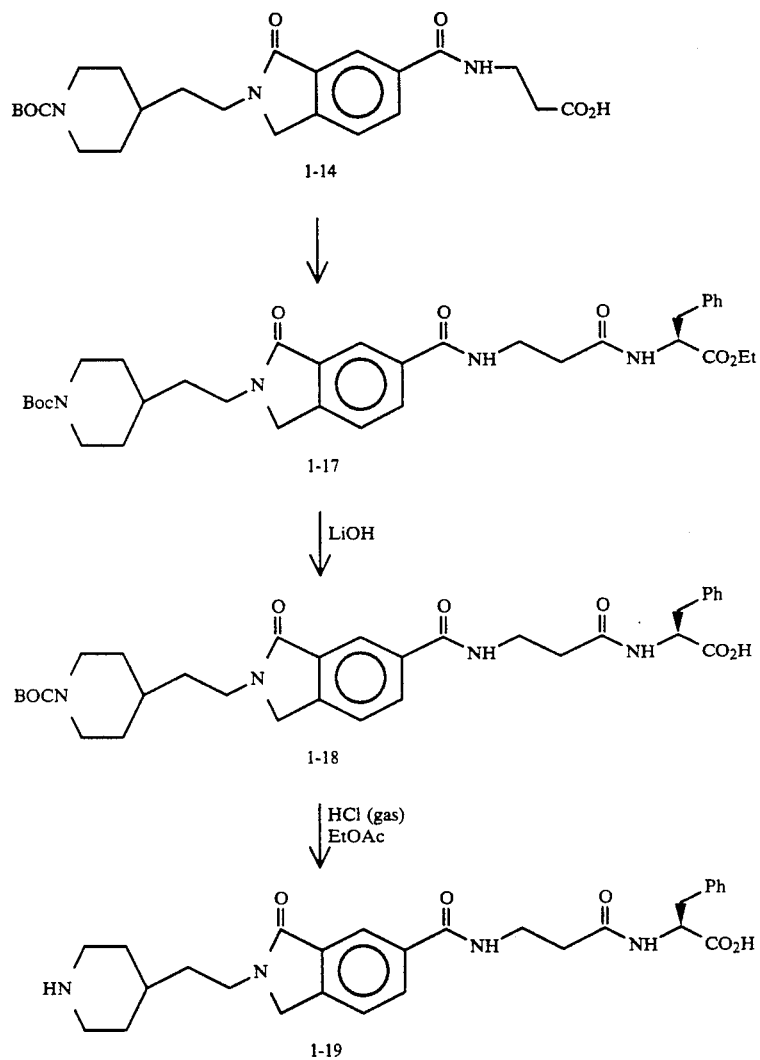

1-H-Isoindole-5-carboxamide, 2,3-dihydro-N-]L-Phe(OEt)-2-(carboxamido)ethyl]-2-[2-(4-N-t-butyloxycarbonylpiperidinyl)ethyl]-3-oxo(1-17)

1-14 (0.35 g, 0.76 mmoles) was treated with L-phenylalanine ethyl ester (2.0 mmoles), N-methylmorpholine (2.0 mmoles) and BOP (0.886 g, 2.0 mmoles), in CH₃CN (5 ml) at room temp for 24 hrs. as described for 6-3. Flash chromatography on silica gel eluting with EtOAc (9)/MeOH (1) gave pure 1-17 as a white solid. R$_f$ 0.3 (silica gel, CHCl₃(2)/acetone (1)).

¹H NMR (300 MHz, CDCl₃) δ 1.28 (3H, t), 1.47 (9H,S), 1.79 (2H, bd), 2.54 (2H, t), 2.72 (2H, m), 3.15 (2H, m) 3.75 (5H, m), 4.20 (4H, m), 4.43 (2H, S), 2.90 (1H, q), 7.12 2H, m), 7.25 (5H, m), 7.54 (1H. d), 8.08 (1H, d), 8.19 (1H, S).

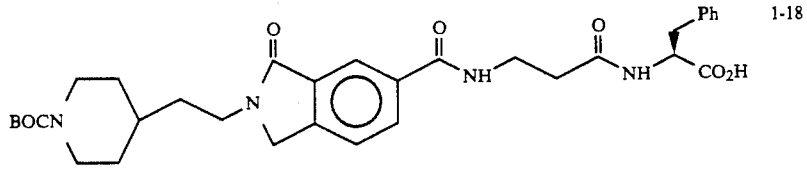

1-H-Isodinole-5-carboxamide, 2,3-dihydro-N[L-Phe-2-(carboxyamido)ethyl]-2-[2-(4-N-t-butyloxycarbonyl-piperidinyl)ethyl]-3-oxo(1-18)

1-17 (0.46 g, 0.72 mmoles) was treated with LiOH.-H₂O (0.152 g, 3.6 mmoles) as described for 1-12 to give 1-18 as a white solid.

¹H NMR (300 MHz, CD₃OD) δ 1.13 (2H, m), 1.43 (9H, s), 1.66 (2H, q), 1.80 (2H, bd), 2.50 (2H, t), 2.70 (2N, M), 2.93 (1H, m), 3.20 (1H, dd), 3.58 (2H, q), 3.70 (2H, t), 4.04 (2H, m), 4.56 (2H, S), 4.68 (1H, m), 7.20 (5H, m), 7.56 (1H, d), 8.02 (1H, d), 8.15 (1H, s).

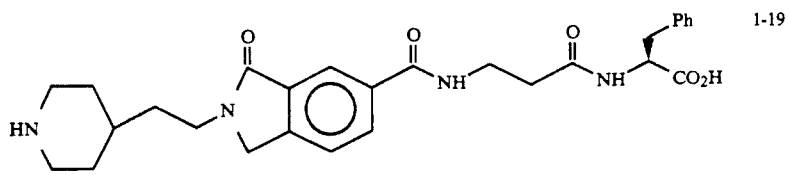

1-H-Isoindole-5-carboxamide, 2,3-dihydro-N[L-Phe-2-(carboxamido)ethyl]-2-[2-(4-piperidinyl)ethyl]-3-oxo (1-19)

1-18 (0.35 g, 0.37 mmoles) was treated with HCl gas as described for 1-13 to give pure 1-19 as a white solid.

¹H NMR (300 MHz, D₂O) δ 1.35 (2H, m), 1.62 (2H, m), 1.93 (2H, m), 2.43 (2H, m), 2.79 (3H, m), 3.07 (1H, m), 3.28 (2H, m), 3.45 (2H, m), 4.50 (2H,S), 6.80 (1H, m), 6.92 (2H, m), 7.00 (2H, m), 7.55 (1H, d), 7.77 (2H, bs).

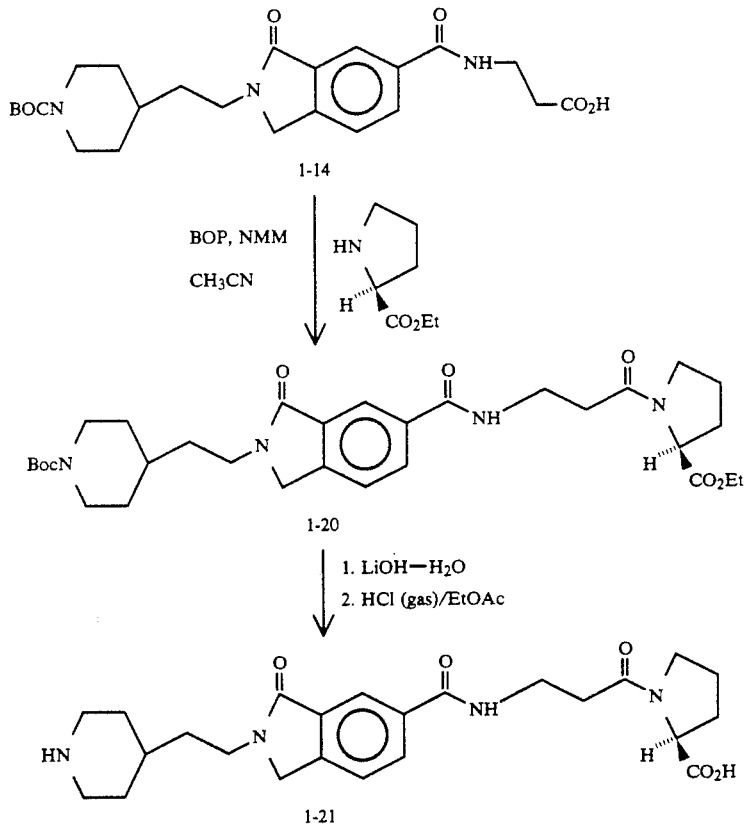

1-H-Isoindole-5-carboxamide, 2,3-dihydro-N-[L-Pro(OEt)-2-(carboxamido)ethyl]-2-[2-(4-N-t-butyloxycarbonylpiperidinyl)ethyl[-3-oxo (1-20)

1-14 (0.35 g, 0.76 mmoles) was treated with L-Proline ethyl ester (0.288 g, 2.0 mmoles), N-methylmorpholine (2.0 mmoles) and BOP (0.886 g, 2.0 mmoles) in CH₃CN (5 ml) as described for 1-17 to give an oily residue. This was purified by flash chromatography on silica gel eluting with acetone (1)/CHCl₃(1) to give pure 1-20.

¹H NMR (300 MHz, CDCl₃) δ 1.16 (2H, m), 1.45 (9H,s), 1.42 (2H, q), 1.65 (2H, bd), 2.03 (2H, m), 2.66 (5H, m), 3.51 (1H, m), 3.67 (2H, m), 3.80 (2H, m), 4.09 (2H, m), 4.20 (2H, q), 4.40 (2H, s), 4.50 (1H, m), 7.41 (1H, m), 7.50 (1H, d), 8.03 (1H, d), 8.19 (1H, s).

1-20 (0.2 g, 0.34 mmoles) was treated with LiOH.H₂O (0.071 g, 1.7 mmoles) as described for 1-12 to give the desired acid.

¹H NMR (300 MHz, CD₃OD) δ 1.15 (2H, m), 1.44 (9H, s), 1.67 (2H, q), 2.80 (2H, bd), 2.25 (1H, m) 2.73 (2H, m), 3.68 (4H, m), 4.06 (2H, m), 4.55 (2H, s), 7.66 (1H, d), 8.05 (1H, d), 8.17 (1H, s).

This acid (0.15 g) was dissolved is EtOAc (10 ml) and treated with HCl gas as described for 1-13 to give pure 1-21 as a white solid.

¹H NMR (300 MHz, D₂O) δ 1.48 (2H, m), 1.67 (1H,

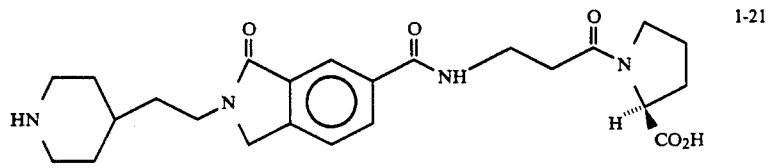

1-H-Isoindole-5-carboxamide, 2,3-dihydro-N-[L-Pro-2-(carboxamido)ethyl]-2-[2-(4-piperidinyl)ethyl]-3-oxo (1-21)

m), 1.76 (2H, m), 2.06 (4H, m), 2.32 (1H, m), 2.62 (1H, m), 2.84 (2H, t), 2.96 (2H, t), 3.43 (2H, d), 3.70 (6H, m), 4.47 (1H, m), 4.66 (2H, s), 7.72 (1H, d), 8.00 (1H, d), 8.09 (1H, s).

SCHEME 2

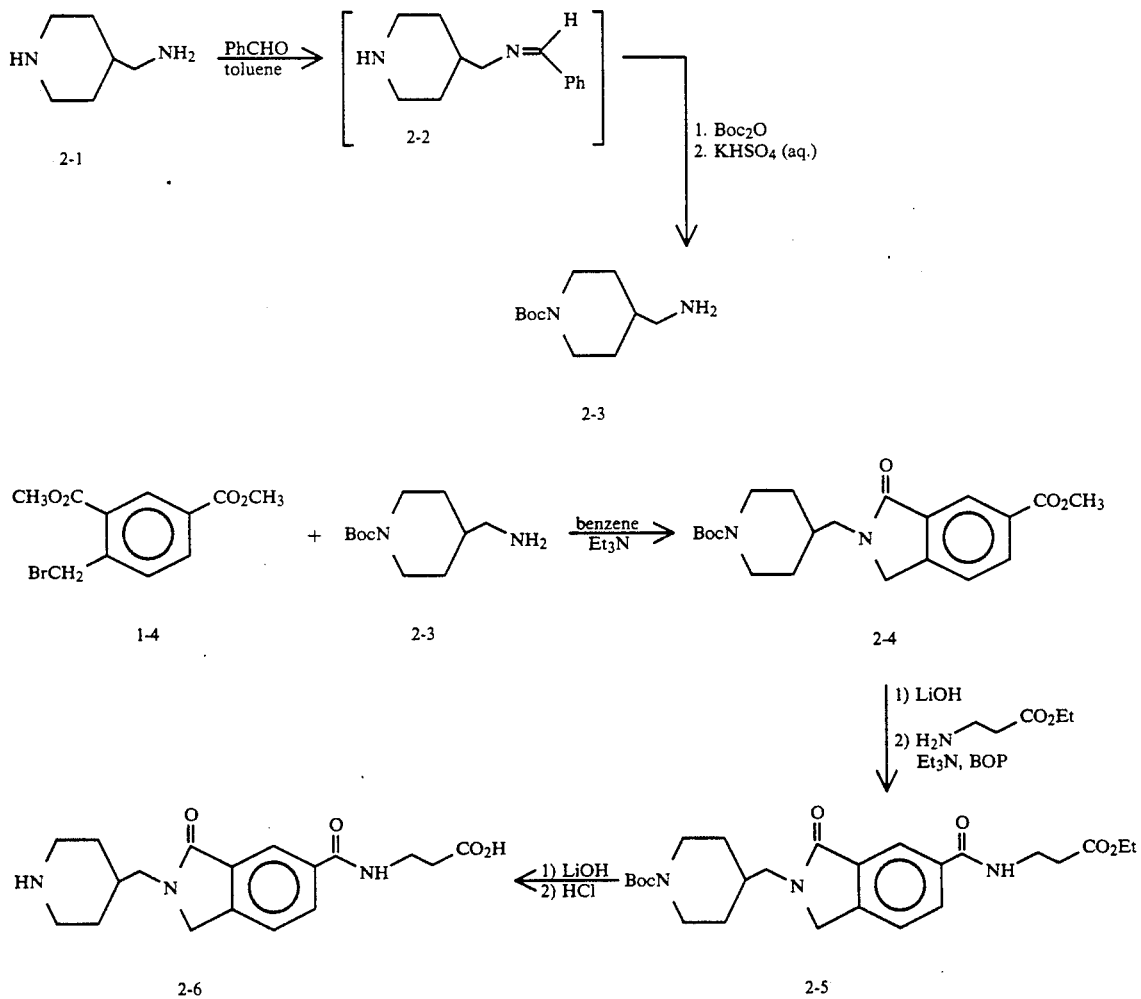

-continued
SCHEME 2

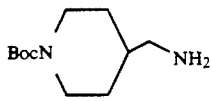

2-3

4-(N-t-Butyloxycarbonylpiperidinyl)methylamine (2-3)

A solution of 4-(piperidinyl)methylamine (2-1) (22.8 g, 0.2 mmoles) in toluene (250 ml) was treated with benzaldehyde (21.2 g, 0.2 mmoles) at room temperature and the resulting mixture was heated at reflux for 3 hours with the aid of a Dean-Stark trap for water removal. The cooled reaction mixture containing the desired Schiff's base 2-2 was treated portionwise with di t-butyl dicarbonate (47.96 g, 0.22 moles) and the resulting solution was stirred at room temperature for 16 hours. The solvent was then removed and the residue was cooled to 0°-5° C. and treated with 1N KHSO$_4$ (220 ml) with stirring for 3 hours. The resulting reaction mixture was extracted with ether (3×200 ml) and then made basic with 1N KOH solution and extracted with CHCl$_3$ (4×75 ml). The combined organic extract was washed with brine, dried (Na$_2$SO$_4$) filtered through celite, and the solvent removed to provide pure 2-3 as a clear oil.

$^1$H NMR (300 MHz, CDCl$_3$) δ 1.13 (2H, m), 1.45 (9H, s), 1.60 (1H, m), 1.74 (2H, d), 2.68 (4H, m), 4.15 (2H, bd).

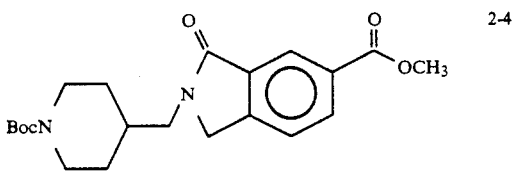

2-4

Methyl-1H-Isoindole-4-carboxylate, 2,3-dihydro-N-[(4-N-t-butyloxycarbonylpiperidinyl)methyl]-3-oxo (2-4)

A solution of 1-4 (3.01 g, 10.5 mmoles) in benzene (20 ml) was treated at room temperature with 2-3 (2.30 g, 10.7 mmoles) and Et$_3$N (10.8 mmoles) and the resulting solution was heated at reflux for 2 hours. The solvent was removed and the residue was taken up in EtOAc (200 ml) and extracted with 10% KHSO$_4$ solution (5×50 ml), brine and dried (MgSO$_4$). Solvent removal gave a residue that was purified by flash chromatography on silica gel eluting with hexane (1)/EtOAc (1) to give pure 2-4 R$_f$0.25.

$^1$H NMR (300 MHz, CDCl$_3$) δ 1.29 (2H, m), 1.45 (9H, s), 1.67 (4H, m), 1.95 (1H, m), 2.70 (2H, t), 3.52 (2H, b), 3.97 (3H, s), 4.13 (2H, b), 4.95 (2H, s), 7.52 (1H, d), 8.23 (1H, d), 8.50 (1H, s).

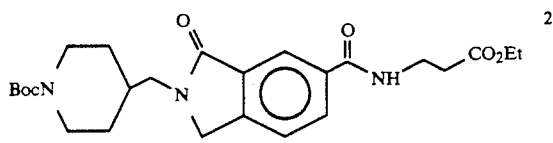

2-5

1-H-Isoindole-5-carboxamide, 2,3-dihydro-N-[2-(carboethoxyethyl)-2-[(4-N-t-butyloxycarbonylpiperidinyl)methyl]-3-oxo (2-5)

A solution of 2-4 (1.92 g, 5.58 mmoles) in 150 ml of THF(1)/MeOH(1)/H$_2$O(1) was treated with LiOH.H$_2$O (1.20 g, 28.6 mmoles) at room temperature and the resulting solution was stirred for 1.0 hr. The solvent was then removed and the residue was taken up in H$_2$O (100 ml) acidified to pH 2 with 10% KHSO$_4$ solution. The desired acid precipitated from solution and was collected.

$^1$H NMR (300 MHz, CD$_3$OD) δ 1.13 (2H, m), 1.40 (9H, s), 1.50-1.65 (3H, m), 2.70 (2H, b), 3.45 (2H, d), 3.98 (2H, d), 4.45 (2H, s), 7.60 (1H, d), 8.10 (1H, d), 8.21 (1H, s).

This acid (1.62 g, 4.91 mmoles) was dissolved in CH$_3$CN (25 ml) and treated at 0° successively with Et$_3$N (34.4 mmoles), β-alanine ethyl ester (5.0 mmoles), and BOP (3.27 g, 7.38 mmoles).

The reaction mixture was then stirred at room temperature for 16 hrs. The solvent was removed and the residue purified by flash chromatography in silica gel eluting with EtOAc (7)/hexane (1) to provide 2-5 as a white solid.

$^1$H NMR (300 MHz, CDCl$_3$) δ 1.27 (6H, m), 1.42 (9H, s), 1.67 (5H, m), 1.95 (1H, m), 2.66 (4H, m), 3.50 (2H, b), 3.74 (2H, g), 4.16 (4H, m), 4.45 (2H, s), 7.00 (1H, t), 7.53 (1H, d), 8.11 (2H, m).

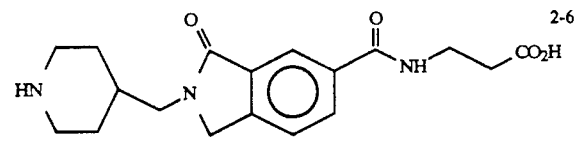

2-6

1-H-Isoindole-5-carboxamide, 2,3-dihydro-N-(2-carboxyethyl)-2-[(4-piperidinyl)methyl]-3-oxo (2-6)

A solution of 2-5 (0.86 g, 2.0 mmoles) in 60 ml of THF(1)/MeOH(1)/H$_2$O(1) was treated with LiOH.H$_2$O (0.45 g, 10.7 mmoles) at room temperature and the resulting solution was stirred at room temperature for 1.0 hr. The solvent was removed and the residue was dissolved in H$_2$O (25 ml), acidified to pH 2-3 with 10% KHSO$_4$ solution and extracted with EtOAc (4×25 ml). The combined organic extracts were washed with brine, dried (Na$_2$SO$_4$) and the solvent removed to give the desired acid as a white solid.

$^1$H NMR (300 MHz, CD$_3$OD) δ 1.16 (2H, m), 1.39 (9H, s), 1.45 (1H, m), 1.80 (2H, bd), 1.93 (2H, d), 2.58 (2H, t), 2.70 (2H, b), 3.45 (2H, d), 3.57 (2H, t), 4.00 (2H, m), 7.59 (1H, d), 8.00 (1H, d), 8.09 (1H, s).

This acid (0.80 g, 1.89 mmoles) was treated with HCl gas in EtOAc solution as described for 2-3 to provide pure 2-6 as a white solid.

$^1$H NMR (300 MHz, CD$_3$OD) δ 1.43 (2H, m), 1.85 (2H, m), 2.10 (1H,m), 2.56 (2H, t), 2.90 (2H, t), 3.34 (2H, bd), 3.54 (4H, m), 4.52 (2H, s), 7.61 (1H, d), 8.00 (1H, d), 8.10 (1H, s).

2-5 can also be converted to 2-7 as shown below:

Treatment of 2-5 (0.90g, 2.09 mmoles) in EtOAc with HCl gas as described for 1-12 gave 2-7 as an white, solid.

$^1$H NMR (300 MHz, CD$_3$OD) δ 1.09 (3H, t), 1.45 (2H, m), 1.86 (2H, bd), 2.13 (2H, m), 2.60 (2H, t), 2.90 (2H, t), 3.32 (2H, bd), 3.56 (4H, m), 4.08 (2H, q), 4.56 (2H, s), 7.62 (1H, d), 8.00 (1H, d), 8.09 (1H, s).

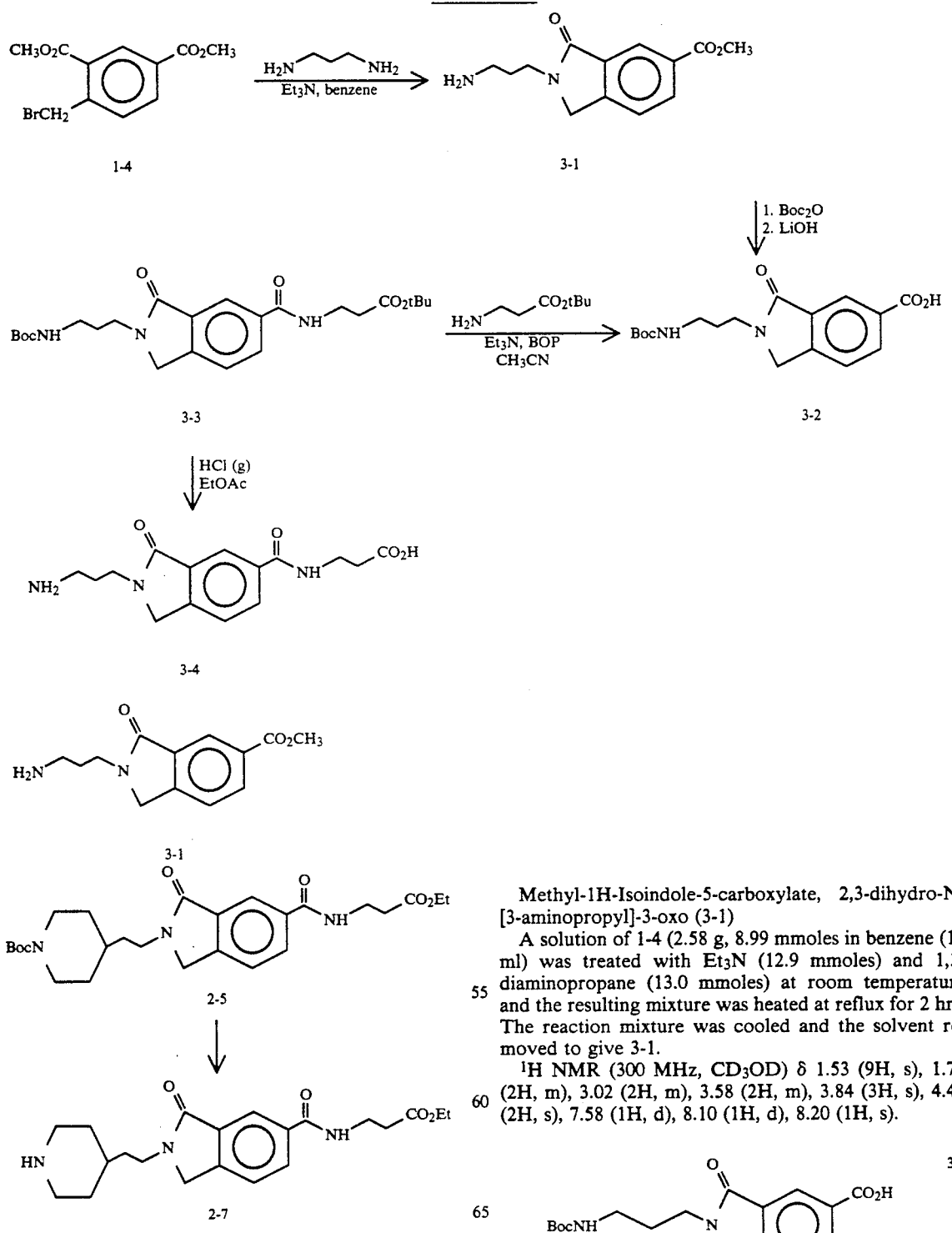

Methyl-1H-Isoindole-5-carboxylate, 2,3-dihydro-N-[3-aminopropyl]-3-oxo (3-1)

A solution of 1-4 (2.58 g, 8.99 mmoles in benzene (10 ml) was treated with Et$_3$N (12.9 mmoles) and 1,3-diaminopropane (13.0 mmoles) at room temperature and the resulting mixture was heated at reflux for 2 hrs. The reaction mixture was cooled and the solvent removed to give 3-1.

$^1$H NMR (300 MHz, CD$_3$OD) δ 1.53 (9H, s), 1.79 (2H, m), 3.02 (2H, m), 3.58 (2H, m), 3.84 (3H, s), 4.48 (2H, s), 7.58 (1H, d), 8.10 (1H, d), 8.20 (1H, s).

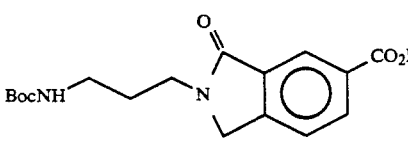

1-H-Isoindole-5-carboxamide,2,3-dihydro-N-[(2-carboethoxy)ethyl]2-[2-(4-piperidinyl)ethyl]-3-oxo(2-7).

1-H-Isoindole-5-carboxylic acid, 2,3-dihydro-N-[3-(N-t-butyloxycarbonylamino)propyl]-3-oxo (3-2)

3-1 (2.22 g, 8.99 mmoles) was suspended in 100 ml of THF(1)/H₂O(1) and treated with Et₃N (9.3 mmoles) and di-t-butyl dicarbonate (4.0 g, 18.3 mmoles) and the resulting mixture was stirred vigorously for 5 hrs. The solvent was removed and the residue was purified by flash chromatography to give the desired protected ester.

¹H NMR (300 MHz, CD₃OD) δ 1.53 (9H, s), 1.80 (2H, m), 3.03 (2H, m), 3.58 (2H, m), 3.86 (3H, s), 4.48 (2H, s), 7.55 (1H, d), 8.10 (1H, d), 8.20 (1H, s).

This ester (0.67 g, 1.93 mmoles) was treated with LiOH.H₂O (0.41 g, 9.76 mmoles) in 60 ml of THF(1)/MeOH(1)/H₂O(1) at room temperature for 1 hr. Solvent removal gave a residue that was dissolved in 25 ml H₂O, acidified to pH 2-3 with 10% KHSO₄ solution and extracted with EtOAc (4×25 ml). The organic extract was washed with brine, dried (MgSO₄) and the solvent removed to give 3-2 as a white solid.

¹H NMR (300 MHz, CD₃OD) δ 1.35 (9H, s), 1.80 (2H, m), 3.04 (2H, t), 3.62 (2H, t), 4.55 (2H, s). 7.62 (1H, d), 8.20 (1H, d), 8.32 (1H, s).

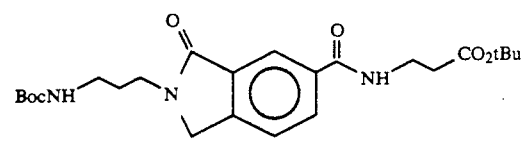

1-H-Isoindole-5-carboxamide, 2,3-dihydro-N-[2 (t-butyloxycarbonyl)ethyl]-2-[3-(N-t-butyloxycarbonylamino)propyl -3-oxo (3-3).

A solution of 3-2 (0.65 g, 1.94 mmoles) in 10 ml CH₃CN was cooled to 0°-10° and treated with Et₃N (13.6 mmoles) and BOP (1.30 g, 2.93 mmoles) and the resulting solution was stirred at room temperature for 16 hrs. The solvent was then removed and the residue was taken up in EtOAc (100 ml) extracted with H₂O (4×25 ml), 10% KHSO₄ solution and dried (MgSO₄). Solvent removal give a residue that was purified by flash chromatography on silica gel eluting with CHCl₃(95)/MeOH(5) to give pure 3-3as a white solid. R_f 0.3 (silica gel, CHCl₃(95)/MeOH(5)).

¹H NMR (300 MHz, CDCl₃), δ 1.46 (9H, s), 1.53 (9H, s), 1.90 (2H, m), 2.62 (2H, t), 3.60 (2H, m), 3.76 (4H, m), 4.50 (2H, s), 7.00 (1H, 6t), 7.62 (1h, d). 8.17 (1H, d), 8.20 (1H, s).

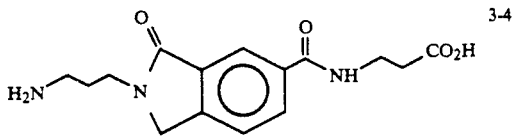

1-H-Isoindole-5-carboxamide, 2,3-dihydro-N-(2-carboxyethyl)-2-3-aminopropyl]-3-oxo (3-4)

3-3 (0.77g, 1.67 mmoles) was suspended in EtOAc (25 ml) and after cooling to −70°, HCl gas was bubbled into the mixture for 5 minutes at which time the reaction mixture was homogeneous. The reaction mixture was then stirred at 0°-5° for 30 minutes. The solvent was removed and the residue was dried at high vacuum to provide pure 3-4 as a white solid.

¹H NMR (300 MHz, CD₃OD) δ 2.00 (2H, m), 2.60 (2H, t) 2.92 (2H, t), 3.59 (2H, m), 3.70 (2H, t), 4.28 (2H, s), 7.63 (1H, d), 8.02 (1H, d), 8.12 (1H, s).

SCHEME 4

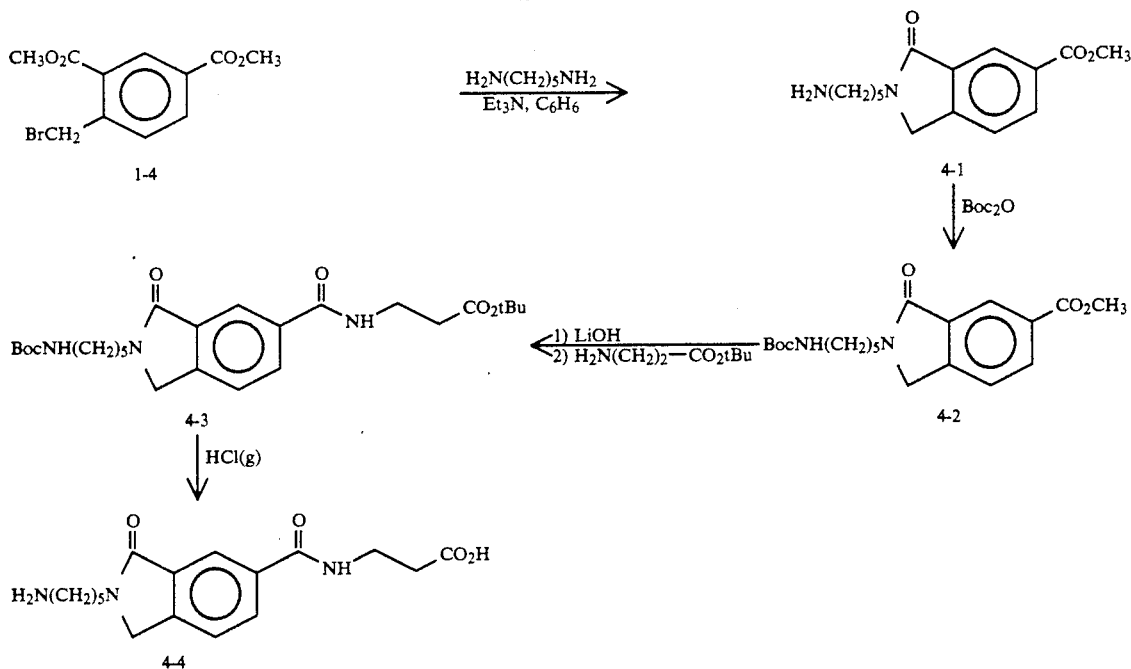

-continued
SCHEME 4

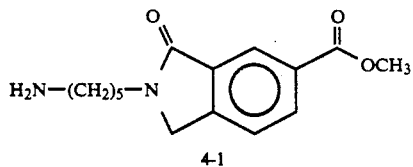
4-1

Methyl-1H-Isoindole-5-carboxylate, 2,3-dihydro N-[5-aminopentyl]-3-oxo (4-1)

A solution of 1-4 (2.56 g, 8.92 mmoles) in benzene (15 ml) was treated with Et₃N (11.5 mmòles) and 1,5-diaminopentane (11.9 mmoles) and the resulting reaction mixture was heated at reflux for 3 hrs. The solvent was then removed and the residue was purified by flash chromatography on silica gel eluting with 25% MeOH in CHCl₃ (MHz) to provide pure 4-1.

¹H NMR (300 MHz, CDCl₃) δ 1.77 (6H, m), 2.45 (2H, bs), 2.71 (2H, t), 3.63 (2H, t), 4.44 (2H, s), 7.52 (1H, d), 8.22 (1H, d), 8.49 (1H, s).

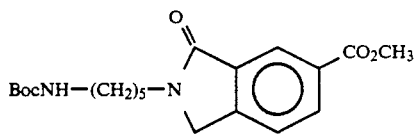
4-2

Methyl-1H-Isoindole-5-carboxylate, 2,3-dihydro-N-[5-(N-t-butyloxycarbonylamino)pentyl]-3-oxo (4-2)

A solution of 4-1 (0.64 g, 2.32 mmoles) in CH₂Cl₂ (10 ml) was treated at room temperature with Et₃N (2.29 mmoles) and Boc₂O (0.74 g, 3.39 mmoles) for 48 hrs. The solvent was then removed and the residue was purified by flash chromatography on silica gel eluting with hexane(7)/acetone(3) to give pure 4-2.

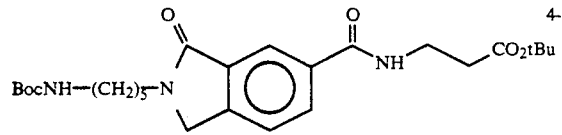
4-3

1-H-Isoindole-5-carboxamide, 2,3-dihydro-N-[2-(2-t-butyloxycarbonyl)ethyl]-2-[5-N-t-butyloxycarbonylamino)pentyl]-3-oxo (4-3)

A solution of 4-2 (0.71g, 1.89 mmoles) in THF(1)/MeOH(1)/H₂O(1) (60 ml) was treated with LiOH.H₂O (0.42 g, 10.0 mmoles) at room temperature for 0.5 hr. The solvent was then removed and the residue was dissolved in H₂O (50 ml), acidified to pH 2-3 with 10% KHSO₄ solution and extracted with EtOAc. The organic phase was washed with brine, dried (MgSO₄) and the solvent removed to give the desired acid.

¹H NMR (300 MHz, CD₃OD) δ 1.30 (9H, s), 1.45 (3H, m), 1.63 (3H, m), 2.92 (2H, t), 3.55 (2H, t), 4.47 (2H, s), 7.58 (1H, d), 8.16 (1H, d). 8.03 (1H, s).

This acid (0.75g, 2.07 mmoles) was dissolved in CH₃CN (15 ml) and was treated at room temperature with β-alanine t-butyl ester (0.39g, 2.54 mmoles), BOP (1.4 g, 3.16 mmoles), Et₃N (6.1 mmoles) and the resulting solution was stirred at room temperature for 20 hrs. The solvent was then removed and the residue was dissolved in EtOAc and extracted with H₂O, 10% KHSO₄ solution and brine. The organic phase was dried (MgSO₄) and was solvent was removed to give a residue that was purified by flash chromatography on silica gel eluting with EtOAc(7)/hexane(3) to give pure 4-3.

¹H NMR (300 MHz, CD₃OD) δ 1.39 (9H, s), 1.45 (2H, m), 1.65 (2H, m), 2.50 (2H, t), 2.96 (2H, q), 3.53 (4H, q), 4.47 (2H, s), 7.58 (1H, d), 7.96 (1H, d), 8.08 (1H, s).

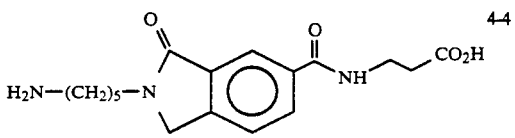
4-4

1-H-Isoindole-5-carboxamide, 2,3-dihydro-N-(2-carboxyethyl)-2-[5-aminopentyl]-3-oxo (4-4)

A solution of 4-3 (0.71g, 1.45 mmoles) in EtOAc (20 ml) was cooled to −78° and treated with HCl gas for 10 minutes. The resulting solution was stirred in at 0° for 0.5 hr. The solvent was removed to provide 4-4 as white solid.

¹H NMR (300 MHz, D₂O) δ 1.29 (2H, m), 1.63 (4H,m), 2.62 (2H,t, 2.87 (2H, t), 3.52 (4H, m), 4.40 (2H, s), 7.51 (1H, d), 7.80 (2H, m).

SCHEME 5

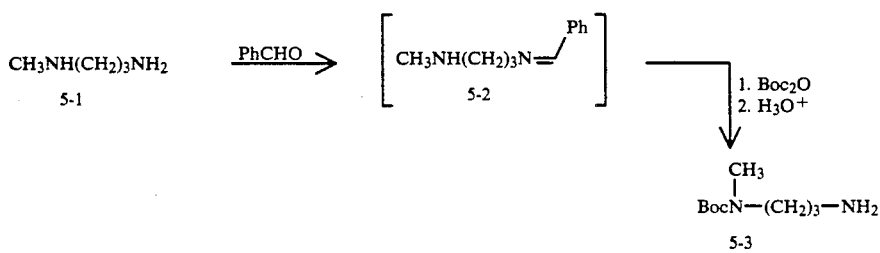

SCHEME 5

-continued

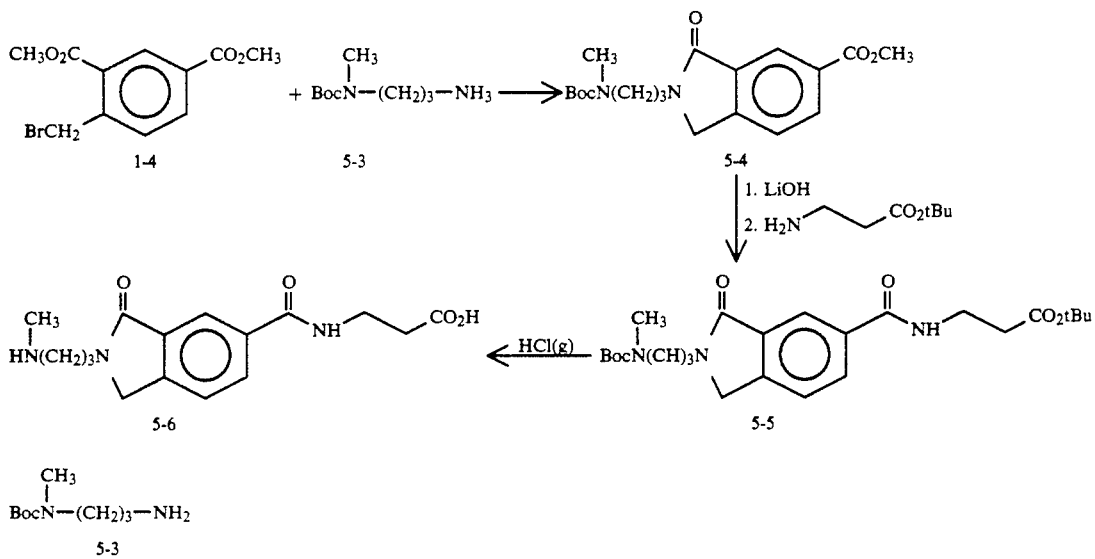

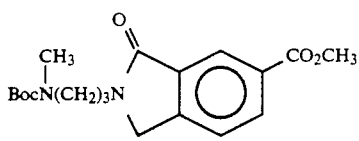
5-3

N-t-Butyloxycarbonyl N-methyl-1,3-diaminopropane (5-3).

A solution of N-methyl-1,3-diaminopropane (2.05 g, 23.2 mmoles) in toluene (30 ml) was treated with benzaldehyde (2.41 g, 22.7 mmoles) and the resulting mixture was heated at reflux with use of a Dean-Stark trap. After 2 hrs. the reaction mixture was cooled and treated with Boc$_2$O (5.57 g, 25.5 mmoles) portionwise and the resulting solution was stirred for 48 hrs.

The solvent was then removed and the residue was cooled to 0°-5° and acidified to PH 2-3 with 10% KHSO$_4$ solution (25 ml) and the resulting slurry was stirred for 3 hrs. This mixture was then extracted with EtOAc and the aqueous phase was adjusted to pH 9 with 1N NaOH and extracted with CHCl$_3$ (5×25 ml). The dried organic phase was concentrated to give 5-3 as an oil.

$^1$H NMR (300 MHz, CDCl$_3$) δ 1.47 (9H, s), 1.72 (2H, bt), 2.16 (2H, bs), 2.75 (2H, t), 2.87 (3H, s), 3.34 (2H, bs).

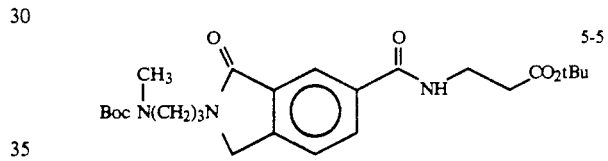

Methyl-1H-Isoindole-5-carboxylate, 2,3-dihydro-N-[2-(3-N-t-butyloxycarbonyl N-methylamino)propyl]-3-oxo (5-4)

A solution of 1-4 (2.0 g, 6.97 mmoles) in benzene (10 ml) was treated with 5-3 (1.19 g, 6.32 mmoles) and Et$_3$N (7.17 mmoles) and the resulting solution was heated at reflux for 24 hrs. The cooled reaction mixture was then dissolved in EtOAc (150 ml), washed with 10% KHSO$_4$ solution (4×50 ml), brine (50 ml) and dried (MgSO$_4$) The solvent was removed to give an oil that was purified by flash chromatography on silica gel eluting with EtOAc(7)/hexane(1) to give pure 5-4 as a white solid.

$^1$H NMR (300 MHz, CDCl$_3$) δ 1.45 (9H, s), 1.92 (2H, m), 2.90 (3H, s), 3.30 (2H, t), 3.68 (2H, t), 3.97 (3H, s), 4.50 (2H, s), 7.55 (1H, d), 8.26 (1H, d), 8.52 (1H, s)

1-H-Isoindole-5-carboxamide, 2,3-dihydro-N-[2-(t-butyloxycarbonyl)ethyl]-2-[3-(N-t-butyloxycarbonyl-N-methylamino)propyl -3-oxo (5-5)

A solution of 5-4 (1.28 g, 3.53 mmoles) in THF(1)/MeOH(1)/H$_2$O(1) (105 ml) was treated with LiOH.H$_2$O (0.76 g. 18.1 mmoles) and the resulting solution was stirred at room temperature for 30 minutes. The solvent was then removed and the residue was taken up in H$_2$O (30 ml), acidified to pH 2-3 with 10% KHSO$_4$ solution, and extracted with EtOAc. The combined organic extracts were washed with brine, dried (MgSO$_4$) and the solvent removed to provide the desired acid.

$^1$H NMR (300 MHz, CD$_3$OD) δ 1.34 (9H,s), 1.86 (2H, m), 2.78 (3H, s), 3.22 (2H, m). 3.55 (2H, t), 4.50 (2H, s), 7.60 (1H, d), 8.17 (1H, d), 8.30 (1H, s).

This acid (1.28 g, 3.59 mmoles) was dissolved in CH$_3$CN (20 ml) and treated successively with β-alanine t-butyl ester hydrochloride (0.65 g, 3.59 mmoles), Et$_3$N (2.51 mmoles), and BOP (2.39 g, 5.40 mmoles) and the resulting cloudy suspension was stirred at room temperature for 20 hrs. The reaction mixture was then concentrated and the residue was taken up in EtOAc (100 ml), extracted with H$_2$O (2×25 ml), 10% KHSO$_4$ solution (4×25 ml), brine and dried (MgSO$_4$). Solvent removal gave a residue that was purified by flash chromatography on silica gel eluting with acetone(3)/hexane(7) to give pure 5-5 as a white solid.

$^1$H NMR (300 MHz, CDCl$_3$) δ 1.42 (9H,s), 1.44 (9H, s), 1.93 (2H, m), 2.37 (2H, t), 2.88 (3H, s), 3.30 (2H, t), 3.68 (4H, m), 4.47 (2H, s), 6.98 (1H, bt), 7.55 (1H, d), 8.09 (1H, d), 8.12 (1H, s).

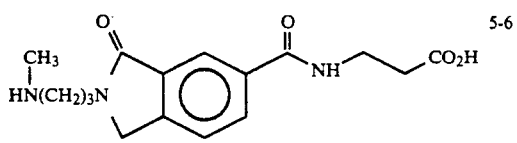
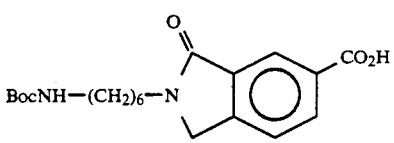

1-H-Isoindole-5-carboxamide, 2,3-dihydro N-(2-carboxyethyl)-(2-[[3-(N-methylamino)propyl]-3-oxo (5-6)

A solution of 5-5 (1.42 g, 2.09 mmoles) in EtOAc (40 ml) was cooled to −78° and treated with HCl gas for 3-5 minutes. The resulting solution was stirred at 0° for 0.5 hr. The solvent was then removed to provide 5-6 as a white solid.

$^1$H NMR (300 MHz, D$_2$O) δ 2.00 (2H, m), 2.62 (5H, m), 3.00 (2H, t), 3.60 (4H, m), 4.29 (2H, s), 7.75 (1H, d), 7.83 (1H, d), 7.88 (1H, s).

1-H-Isoindole-5-carboxylic acid, 2,3-dihydro-N-[6-N(t-butyloxycarbonylamino)hexyl]-3-oxo (6-2)

Treatment of 6-1 with Boc$_2$O (1 equiv) and triethylamine (2 equivalents) in H$_2$O(1)/THF(1) (100 ml) at room temperature for 48 hours followed by solvent removal gave crude BOC-protected derivative. Hydrolysis of this with LiOH.H$_2$O (4 equiv.) as described for 1-10 gave 6-2 as an oil.

$^1$H NMR/(300 MHz, CD$_3$OD) δ 1.32 (17H, m), 1.68 (2H, m) 2.95 (2H, t), 4.50 (2H, s), 7.62 (1H, d), 8.19 (1H, d). 8.31 (1H, s).

SCHEME 6

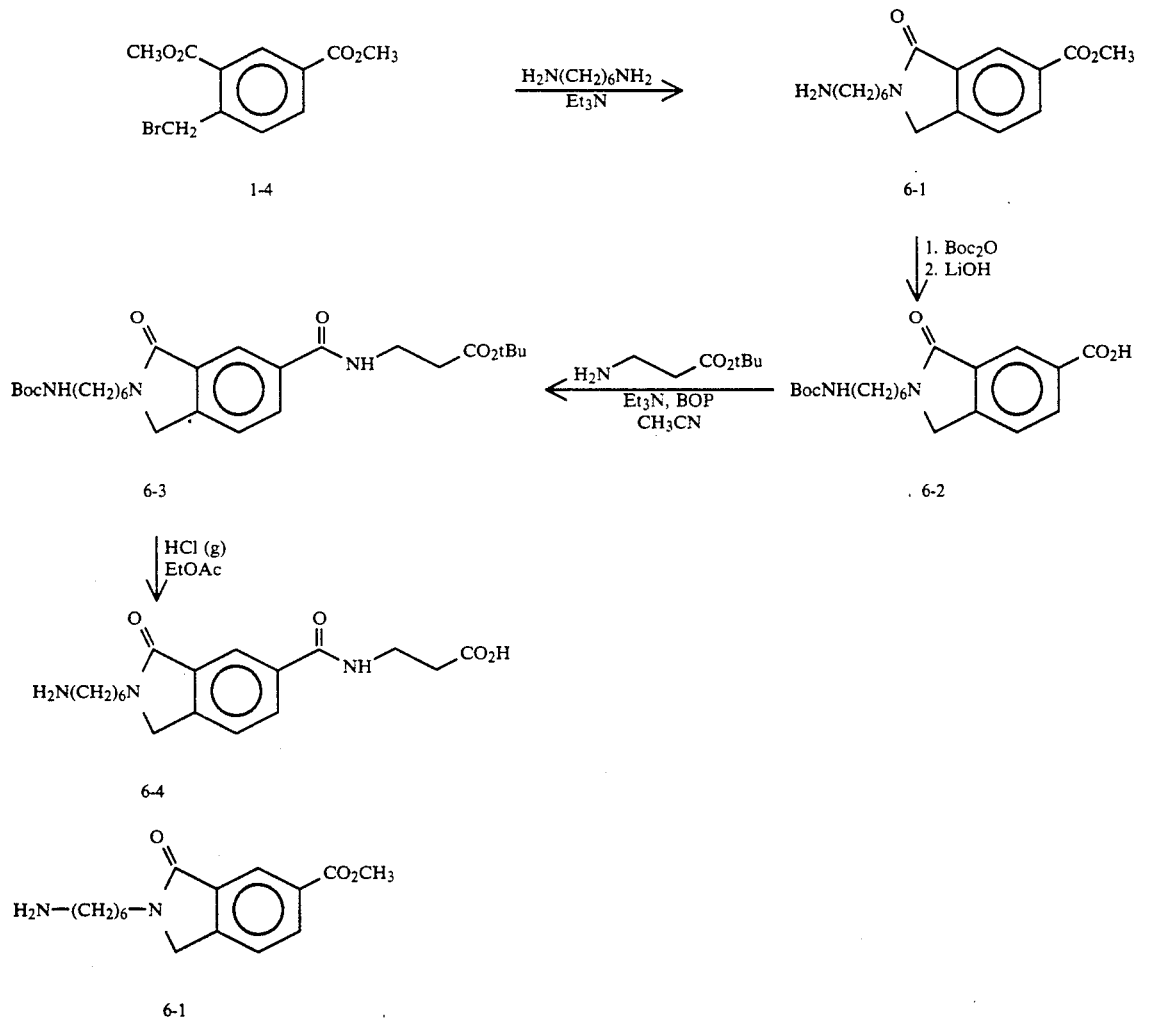

Methyl-1H-Isoindole-5-carboxylate, 2,3-dihydro-N-[6-aminohexyl]-3-oxo (6-1)

Treatment of 1-4 with 1,6-diaminohexane as described for 1-9 provided 6-1 as a white solid. R$_f$ 0.5 (silica gel, hexane (9)/EtOAc (1).

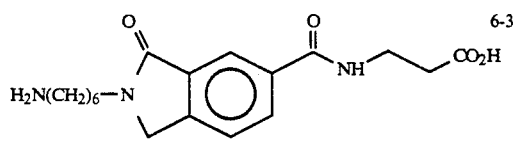

1-H-Isoindole-5-carboxamide, 2,3-dihydro-N-[2-(t-butyloxycarbonyl)ethyl]-2-[6-N-(t-butyloxycarbonylamino)hexyl]-3-oxo (6-3)

¹H NMR (300 MHz, CD₃OD) δ 1.42 (4H, m), 1.68 (4H, m), 2.63 (2H, t), 2.88 (2H, t), 3.60 (4H, m), 4.52 (2H, s), 7.60 (1H, d), 7.97 (1H, d), 8.10 (1H, s).

SCHEME 7

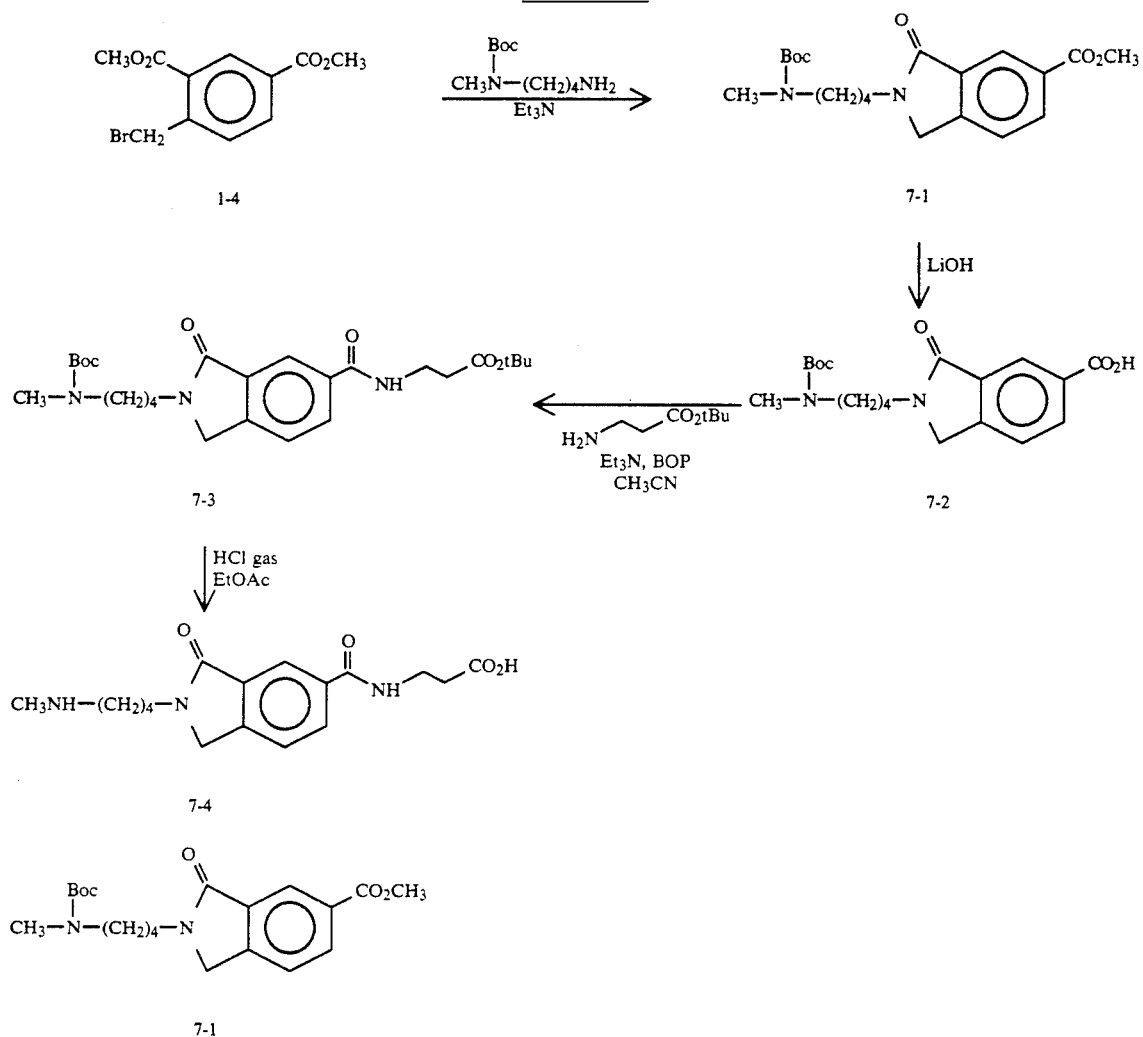

Treatment of 6-2 (1.18 g, 3.12 mmoles) with t-butyl β-alanine (0.54 g, 3.51 mmoles) as described for 1-11 gave crude 6-3. This was purified by flash chromatography on silica gel eluting with pet ether (6)/EtOAc (4) to provide 6-3 as an oil. R_f 0.25 (silica gel, pet ether (7)/acetone (3)).

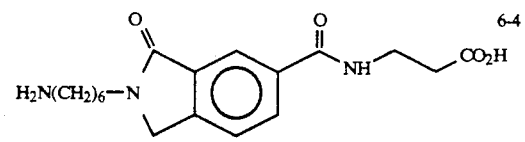

1-H-Isoindole-5-carboxamide,2,3-dihydro N-(2-carboxyethyl)-2-[6-aminohexyl]-3-oxo (6-4)

6-3 (0.44 g) was dissolved in EtOAc (25 ml) cooled to −78− and treated with HCl gas for 5 minutes. The reaction mixture was then stirred at 0° for 30 minutes and the solvent was removed. The residue was purified by flash chromatography on silica gel eluting with EtOH(9)/H₂O(1)/NH₄OH(1) to provide 6-4 as a white solid.

Methyl-1H-Isoindole 5-carboxylate, 2,3-dihydro-N-[4-(N-methyl-N-t-butyloxycarbonylamino)butyl]-3-oxo (7-1)

Treatment of 1-4 with 4-(N-methyl-N-t-butyloxycarbonylamino)butylamine (prepared as described for 5-3) as described for 1-9 provided crude 7-1. This was purified by flash chromatography on silica gel eluting with EtOAc(7)/hexane(3) to give pure 7-1. R_f 0.3 (silica gel, EtOAc(7)/hexane(3).

¹H NMR (300 MHz, CDCl₃) δ 1.45 (9H, s), 1.60 (4H, m), 7.52 (1H, d), 8.23 (1H, d), 8.23 (1H, d), 8.50 (1H, s).

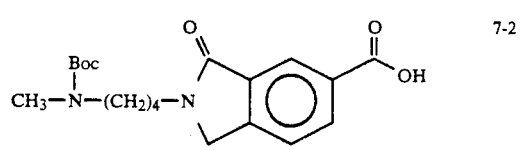

1H-Isoindole-5-carboxylic acid, 2,3-dihydro-N-[4-(N-methyl-N-t-butyloxycarbonylamino)butyl]-3-oxo (7-2)

Treatment of 7-1 (1.16 g, 2.08 mmoles) with LiOH.H$_2$O (0.65 g, 15.5 mmoles) in THF(1)/CH$_3$OH(1)/H$_2$O(1) (75 ml) as described for 1-10 gave 7-2 as a white solid.

$^1$H NMR (300 MHz, CD$_3$OD) δ 1.67 (10H, m), 1.80 (2H, m), 1.89 (2H, m), 3.05 (3H, s). 3.50 (2H, t), 3.88 (2H, t), 4.78 (2H, s), 7.90 (1H, d), 8.45 (1H, d), 8.60 (1H, s).

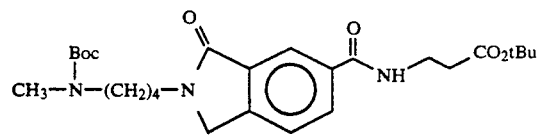

1-H-Isoindole-5-carboxamide, 2,3-dihydro-N-[2-(t-butyloxycarbonyl)ethyl]-2-[4-(N-t-butyloxycarbonyl-N-methylamino)butyl]-3-oxo (7-3)

Treatment of 7-2 (1.04 g, 2.86 mmoles) with β-alanine t-butyl ester (0.54 g, 2.97 mmoles) as described for 1-11 gave crude 7-3. This was purified by flash chromatography on silica gel eluting with hexane(6)/acetone(4) to give 7-3 as an oil. R$_f$ 0.4 (silica gel, EtOAc(7)/hexane(3)).

$^1$H NMR (300 MHz, CHCl$_3$) δ 1.46 (18H, m), 1.60 (4H, m), 2.58 (2H, t), 2.83 (3H, s), 3.28 (2H, t), 3.70 (4H, m), 4.45 (2H, s), 7.52 (1H, d), 8.09 (1H, d), 8.11 (1H, s).

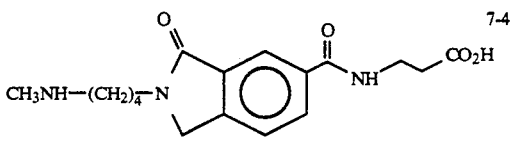

1-H-Isoindole-5-carboxamide, 2,3-dihydro-N-(2-carboxyethyl)-2-[4-(N-methylamino)butyl]-3-oxo (7-4)

Treatment of 7-3 with HCl gas in EtOAc solution as described for 6-4 gave 7-4 as a white solid.

$^1$H NMR (300 MHz, CD$_3$OD) δ 1.67 (4H, m), 2.58 (5H, m), 2.95 (2H, t), 3.50 (4H, m), 4.50 (2H, s), 7.56 (1H, d), 7.97 (1H, d), 8.08 (1H, s).

SCHEME 8

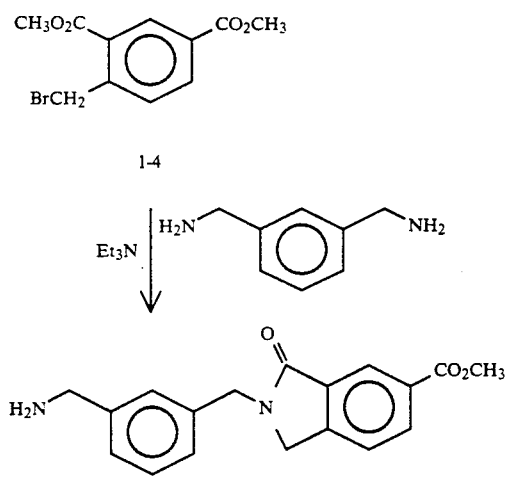

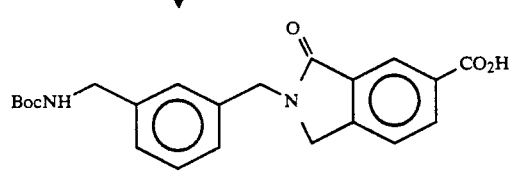

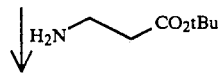

SCHEME 8 -continued

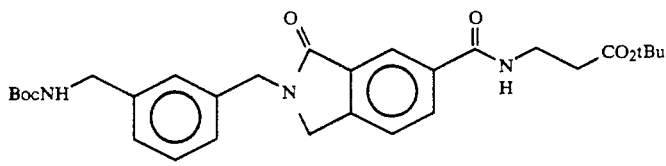

8-3

↓ HCl gas
EtOAc

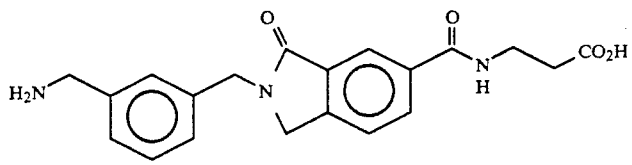

8-4

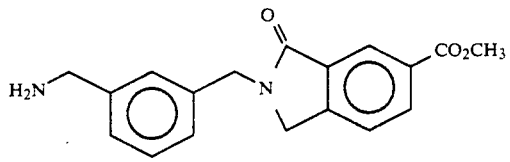

8-1

Methyl-1H-Isoindole-5-carboxylate, 2,3-dihydro-N-[(3-aminomethylphenyl)methyl]-3-oxo (8-1)

Treatment of 1-4 (2.15 g, 7.49 mmoles) with m-xylenediamine (9.85 mmoles) as described for 1-9 gave crude 8-1. This was purified by flash chromatography on silica gel eluting with $CH_3OH$ (10/$CHCl_3$ ($NH_4OH$) (90) to give pure 8-1 as a white solid. $R_f$ 0.7 silica gel, $CH_3OH$ (10)/$CHCl_3$ ($NH_4OH$) (90).

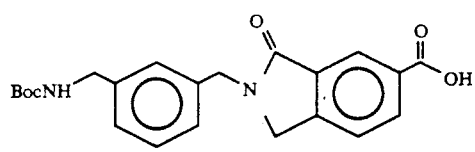

8-2

1-H-Isoindole-5-carboxylic acid, 2,3-dihydro-N-[(3-N-t-butyloxycarbonylaminomethylphenyl)methyl]-3-oxo (8-2)

8-1 (1.76 g, 5.67 mmoles) was dissolved in $CH_2Cl_2$ (25 ml) and treated with $Boc_2O$ (1.50 g, 6.87 mmoles) and $Et_3N$ (6.45 mmoles) as described for 6-2 to give the desired N-protected ester. $R_f$ 0.25 (silica gel, EtOAc (1)/hexane (1)).

$^1H$ NMR (300 MHz, $CDCl_3$) δ 1.45 (9H, s), 1.65 (1H, m), 2.06 (2H, s), 4.30 (4H, m), 4.81 (2H, s), 7.27 (6H, m), 7.47 (1H, d), 8.22 (1H, d), 8.55 (1H, s).

This acid was treated with $LiOH.H_2O$ as described for 6-2 to provide 8-2 as a white solid. $R_f$ 0.1 (silica gel, $CHCl_3$ (97)/$CH_3OH$ (1)/HOAc ()). $^1H$ NMR (300 MHz, $CD_3OD$) δ 1.32 (9H, s), 4.12 (2H, s), 4.38 (2H, s), 4.73 (2H, s), 7.12 (4H, m), 7.25 (1H, m), 7.52 (1H, d).

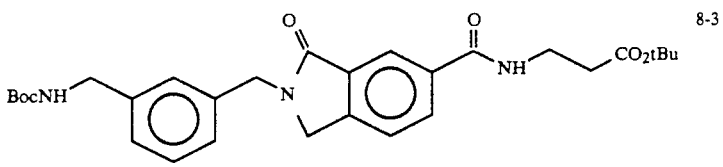

8-3

1H-Isoindole-5-carboxamide, 2,3-dihydro-N-[2-(t-butyloxycarbonyl)ethyl]2-[(3-N-t-butyloxycarbonylaminomethylphenyl)methyl]-3-oxo (8-3)

Treatment of 8-2 (0.80 g, 2.02 mmoles) with β-alanine t-butyl ester (0.35 g, 2.28 mmoles), BOP (1.35 g, 3.04 mmoles) and $Et_3N$ (14.3 mmoles) as described for 1-11 gave crude 8-3. This was purified by flash chromatography on silica gel eluting with hexane (6)/acetone (4) to give pure 8-3.

$^1H$ NMR (300 MHz, $CDCl_3$) δ 1.45 (9H, s), 1.47 (9H, s), 2.59 (2H, t), 3.72 (2H, m), 4.30 (4H, s), 4.82 (2H, s), 4.88 (1H, m), 7.28 (5H, m), 7.48 (1H, d), 8.08 (1H, d), 8.19 (1H, s).

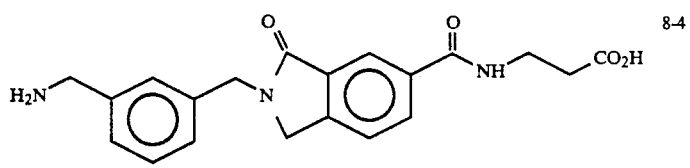

1-H-Isoindole-5-carboxamide, 2,3-dihydro N-(2-carboxyethyl)-2-[(3-aminomethylphenyl)methyl]-3-oxo (8-4)

8-3 (0.872 g, 1.67 mmoles) was dissolved in EtOAc (25 ml) and treated with HCl as described for 6-4 to give pure 8-4.

$^1$H NMR (300 MH$_3$, CD$_3$OD) δ 2.58 (2H, t), 3.56 (2H, t), 4.00 (4H, s), 4.42 (2H, s), 7.32 (4H, m), 7.52 (1H, d), 7.95 (1H, d), 8.11 (1H, s).

SCHEME 9

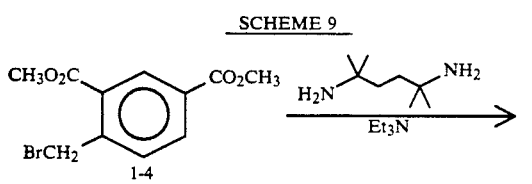

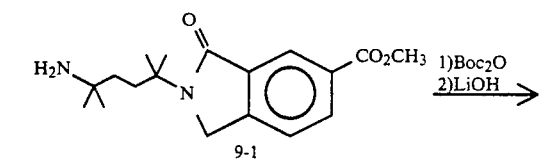

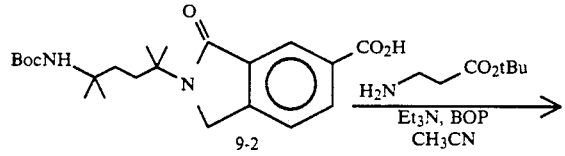

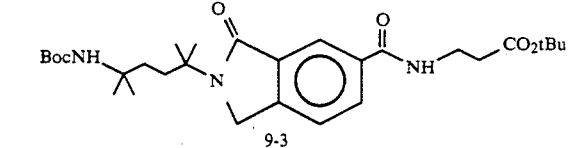

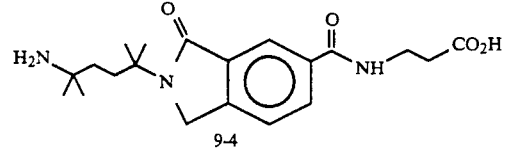

Methyl-1H-Isoindole-5-carboxylate, 2,3-dihydro-N-[(4-amino-1,1,4,4-tetramethyl)butyl]-3-oxo (9-1)

Treatment of 1-4 (2.51 g, 8.74 mmoles) with 1,1,4,4, tetramethyl 1,4-diaminobutane (1.50 g, 10.40 mmoles) as described for 1-9 provided 9-1. R$_f$ 0.25 silica gel, 10% CH$_3$OH in CHCl$_3$/NH$_4$OH.

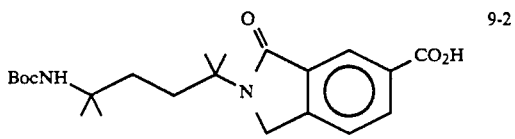

1-H-Isoindole-5-carboxylic acid, 2,3-dihydro-N-[(4-N-t-butyloxycarbonylamino)-1,1,4,4-tetramethyl)-butyl]-3-oxo (9-2)

9-1 was treated with Boc$_2$O and Et$_3$N as described for 6-2 to give the desired Boc protected ester. R$_f$ 0.3 (silica gel, hexane (7)/acetone/3).

This ester (1.03 g, 2.46 mmoles) was treated with LiOH.H$_2$O (0.54 g, 12.9 mmoles) in THF (1)/CH$_3$OH (1)/H$_2$O (1) (60 ml) as described for 6-2 to give pure 9-2. R$_f$ 0.35 (silica gel, EtOAc).

$^1$H NMR (300 MHz, CD$_3$OD) δ 1.10 (6H, s), 1.28 (9H, s), 1.48 (6H, s), 4.60 (2H, s), 7.55 (1H, d), 8.16 (1H, d), 8.26 (1H, s).

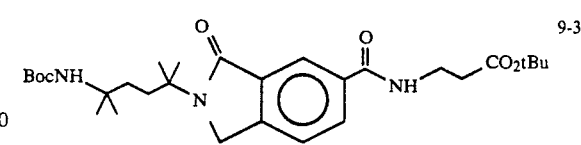

1-H-Isoindole-5-carboxamide, 2,3-dihydro-N-[2-t-butyloxycarbonyl)ethyl]-2-[4-(N-t-butyloxycarbonylamino)-(1,1,4,4-tetramethyl)butyl]-3-oxo (9-3)

9-2 (1.05 g, 2.83 mmoles) was treated with β-alanine t-butyl ester (0.48 g, 3.12 mmoles), Et$_3$N (20.0 mmoles) and BOP (1.91 g, 4.31 mmoles) in CH$_3$CN (15 ml) as described for 1-11 to provide crude 9-3. This was purified by flash chromatography on silica gel eluting with pet ether (7)/acetone (3) to give Pure 9-3. R$_f$ 0.3 silica gel, pet ether (7)/acetone (3).

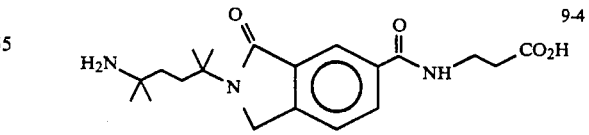

1-H-Isoindole-5-carboxamide, 2,3-dihydro-N-(2-carboxyethyl)-2-[(4-amino-1,1,4,4-tetramethyl)butyl]-3-oxo (9-4)

9-3 (1.23 g) was dissolved in EtOAc (25 ml). cooled to −78° and treated with HCl gas as described for 6 4 to give pure 9-4.

$^1$H NMR (300 MHz, CD$_3$OD) δ 1.26 (6H, s), 1.53 (8H, m), 2.59 (2H, t), 3.57 (2H, m), 4.63 (2H, s), 7.57 (1H, d), 7.98 (1H, d), 8.06 (1H, s).

SCHEME 10

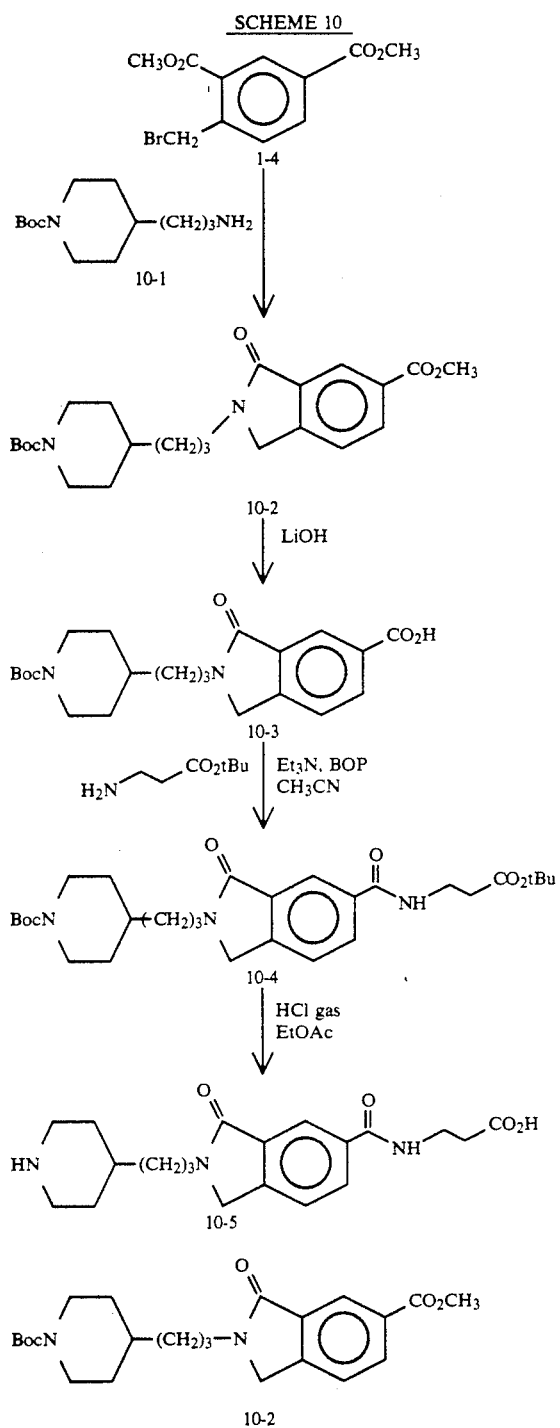

Methyl-1H-Isoindole-5-carboxylate, 2,3-dihydro-N-[3-(4-N-t-butyloxycarbonylpiperidinyl)propyl]-3-oxo (10-2)

Treatment of 1-4 (4.59 g, 16.0 mmoles) with 3-(4-N-t-butyloxycarbonylpiperidinyl)propylamine (prepared from 1-6 by nitrile formation followed by catalytic hydrogenation) (4.36 g, 15.6 mmoles) as described for 1-9 gave crude 10 2. This was purified by flash chromatography on silia gel eluting with hexane (3)/ethyl acetate (1) to give pure 10-2.

$^1$H NMR (300 MHz, CDCl$_3$) δ 1.10 (2H, m), 1.30 (2H, m), 1.45 (9H, s), 1.68 (4H, m), 2.66 (2H, m), 3.62 (2H, t), 3.95 (3H, s), 4.10 (2H, m), 4.44 (2H, s), 7.52 (1H, d), 8.23 (1H, d), 8.50 (1H, s).

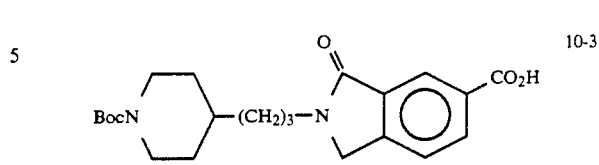

1-H-Isoindole-5-carboxylic acid, 2,3-dihydro-N-[3-(4-N-t-butyloxycarbonylpiperidinyl)propyl]-3-oxo (10-3)

Treatment of 10-2 (2.79 g, 6.91 mmoles) with LiOH.H$_2$O (1.48 g, 35.2 mmoles) in THF (1)/MeOH (1)/H$_2$O (1) as described for 1-10 provided 10-3 as a white solid.

$^1$H NMR (300 MHz, CD$_3$OD) δ 0.95 (2H, m), 1.23 (3H, m), 1.35 (9H, s), 1.66 (3H, m), 2.65 (2H, m), 3.56 (2H, t), 3.96 (2H, bd), 4.50 (2H, s), 7.60 (1H, d), 8.17 (1H, d), 8.30 (1H, s)

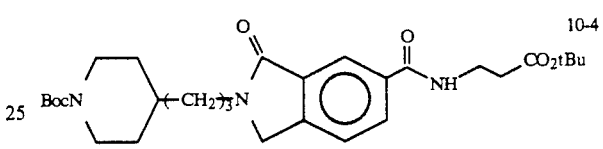

1-H-Isoindole-5-carboxamide, 2,3-dihydro-N-[3-(t-butyloxycarbonyl)ethyl]-2-[3-(4-N-t-butyloxycarbonylpiperidinyl)propyl]-3-oxo (10-4)

Treatment of 10-3 (1.28 g, 3.28 mmoles) with β-alanine t-butyl ester (0.64 g, 3.52 mmoles), Et$_3$N (3.3 mmoles), BOP (2.16 g) in CH$_3$CN as described for 1-11 gave crude 10-4. This was purified by flash chromatography on silica gel eluting with hexane (7)/acetone (3) to give pure 10-4.

$^1$H NMR (300 MHz, CDCl$_3$) δ 1.09 (2H, m), 1.30 (3H, m), 1.45 (9H, s), 1.68 (4H, m), 2.62 (4H, m), 3.62 (2H, t), 3.70 (2H, t), 4.08 (2H, bd), 4.23 (2H, s), 7.52 (1H, d), 8.10 (1H, d), 8.13 (1H, s).

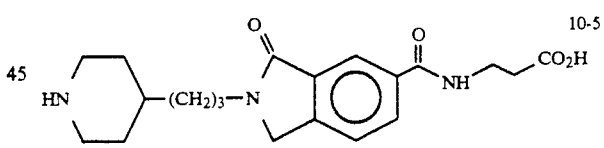

1-H-Isoindole-5-carboxamide, 2,3-dihydro-N-(2-carboxyethyl)-2-[3-(4-piperidinyl)propyl]-3-oxo (10-5)

Treatment of 10-4 (1.18 g) in EtOAc (30 ml) −78° with HCl gas as described for 6-4 gave pure 10-5 as a white solid. R$_f$ 0.4 (silica gel, EtOAc).

$^1$H NMR (300 MHz, CD$_3$OD) δ 1.30 (4H, m), 1.67 (4H, m), 1.89 (2H, bd), 2.60 (2H, t), 2.40 (2H, t), 3.19 (2H, bd), 3.58 (4H, m), 4.50 (2H, s), 7.60 (1H, d), 7.99 (1H, d), 8.08 (1H, s).

SCHEME 11

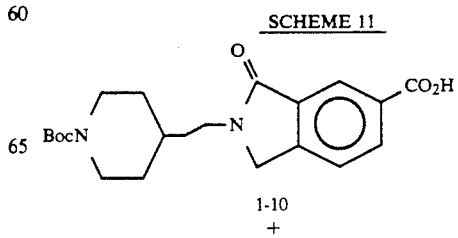

1-10
+

-continued
SCHEME 11

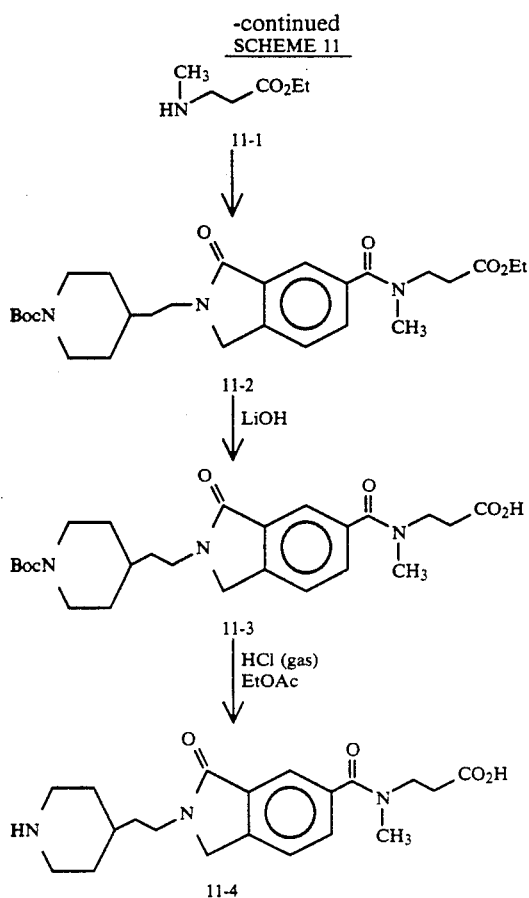

1-H Isoindole-5-carboxamide, 2,3-dihydro-N-[N-methyl-N-2-(carboethoxy)ethyl]-2-[2-(4-N-t-butyloxycarbonylpiperidinyl)ethyl]-3-oxo (11-2)

Treatment of 1-10 (0.2 g, 0.54 mmoles) with ethyl 3-(N-methyl)aminopropionate (0.14 g, 1.08 mmoles) (Appl. Polymer Sci., 1969, 13, 227), N-methylmorpholine (1.08 mmoles), and BOP (0.35 g, 0.8 mmoles) in CH$_3$CN (3 ml) as described for 1-11 gave crude 11-2. This was purified by flash chromatography on silica gel eluting with EtOAc to give pure 11-2 as a white solid.

$^1$H NMR (300 MHz, CD$_3$OD) δ 1.20 (6H, m), 1.45 (9H, s), 1.67 (2H, q), 1.80 (2H, bd), 2.73 (2H, m), 3.00 (3H, s), 3.08 (1H, bs), 3.71 (2H, t), 3.84 (1H, m), 4.05 (4H, m), 4.17 (1H, m), 4.56 (2H, s), 7.66 (2H, m), 7.77 (1H, s).

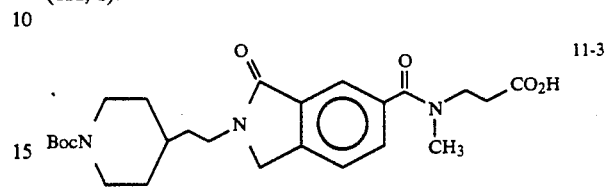

1H-Isoindole-5-carboxamide, 2,3-dihydro N-[N-methyl-N-(2-carboxyethyl)]-2-[2-(4-N-t-butyloxycarbonylpiperidinyl)ethyl]-3-oxo (11-3)

11-2 (0.23 g, 0.49 mmoles) was treated with LiOH.H$_2$O (0.096 g, 2.3 mmoles) as described for 8-2 to give 11-3 as a white solid.

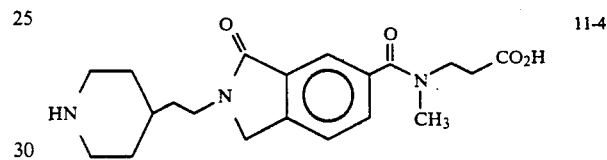

1-H-Isoindole-5-carboxamide, 2,3-dihydro-N-[N-methyl-N-(2-carboxyethyl)]-2-[(4-piperidinyl)ethyl]-3-oxo (11-4)

11-3 (0.2 g, 0.45 mmoles) in EtOAc was treated with HCl gas as described for 8-4 to give pure 11-4 as a white solid.

$^1$H NMR (300 MHz, CD$_3$OD) δ 1.14, 1.37 1.50 (1H, m), 1.63 (2H, q), 1.92 (2H, bd), 2.51 (1H, t), 2.67 (1H, t), 2.83 (2H, m), 3.31 (2H, bd), 3.54 (1H, t), 3.60 (2H, t), 3.73 (1H, t), 4.49 (2H, s), 7.57 (2H, q), 7.65 (1H, s).

SCHEME 12

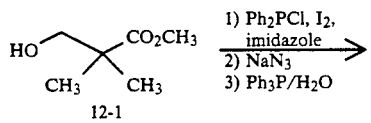

1) Ph$_2$PCl, I$_2$, imidazole
2) NaN$_3$
3) Ph$_3$P/H$_2$O

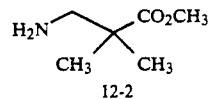

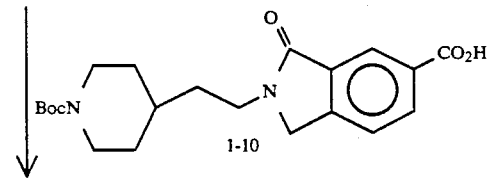

SCHEME 12

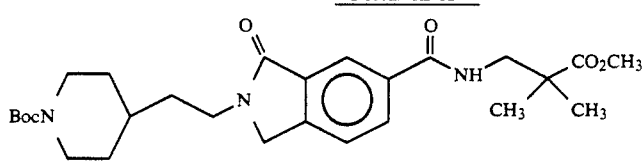

12-3

↓ 1. LiOH
↓ 2. HCl gas

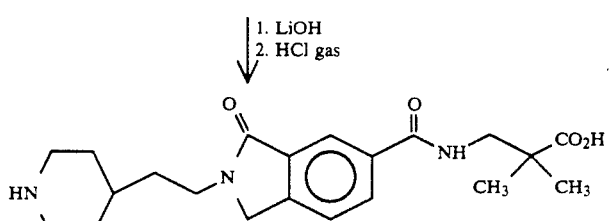

12-4

Methyl 3-amino-2,2-dimethylpropionate (12-2)

12-1 (Aldrich, 5.0 g, 38 mmoles) in toluene (150 ml) at room temperature was treated with chlorodiphenyl phosphine (49.4 mmoles) followed by imidazole (5.7 g, 83.6 mmoles) and $I_2$ (12.5 g, 49.4 mmoles) and the resulting brown solution was stirred for 0.5 hours. This mixture was poured into 150 ml saturated $Na_2CO_3$ solution and the organic layer was separated and washed with saturated $Na_2CO_3$ solvent, 5% $Na_2SO_4$ solution, $H_2O$, and 10% $KHSO_4$ solution. The nearly colorless organic layer was then washed with brine, dried ($Na_2SO_4$) and the solvent was removed to produce a yellow residue. This was purified by flash chromatography on silica gel eluting with hexane (6)/EtOAc (4) to give the desired iodo intermediate as an oil. $R_f$ 0.9 (silica gel, hexane (6)/EtOAc (4)).

$^1$H NMR (300 MHz, CDCl$_3$) δ 1.38 (6H, s), 3.40 (2H, s), 3.75 (3H, s),

This iodo compound (3.9 g, 16 mmoles) was dissolved in DMSO (80 ml) and treated with NaN$_3$ (2.1 g, 32 mmoles) at 70° for 2 hours. The cooled reaction next was diluted with EtOAc and extracted with $H_2O$ and brine. The organic phase was washed with brine, dried (Na$_2$SO$_4$) and the solvent was removed to give the desired azide as a foam.

$^1$H NMR (300 MHz, CDCl$_3$) δ 1.25 (6H, s), 3.45 (2H, s), 3.75 (3H, s).

This azide (2.0 g, 12.7 mmoles) was dissolved in THF (50 ml) and treated with $H_2O$ (25 ml) and triphenyl phosphine (13.3 g, 50.8 mmoles) at room temperature for 2 hours. The THF was removed under vacuum and the resulting residue was acidified to pH 2-3 with 10% KHSO$_4$ solution. This was filtered to remove triphenyl phosphine and the filtrate was extracted with EtOAc. The acidic aqueous phase was then basified with 10% NaOH and extracted with Et$_2$O. The combined ether extracts were washed with brine, dried (Na$_2$SO$_4$) and the solvent removed to give 12-2 as a clear oil. $R_f$ 0.35 (silica gel. CH$_2$Cl$_2$ (9)/CH$_3$OH (1)/H$_2$O (1).

$^1$H NMR (300 MHz, CD$_3$OD) δ 1.22 (6H, s), 2.75 (2H, s). 3.75 (3H, s).

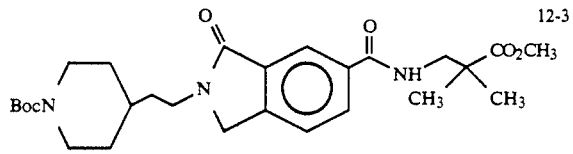

12-3

1-H-Isoindole-5-carboxamide, 2,3-dihydro-N-[(2-carbomethoxy-2-methyl)propyl]-2-[2-(4-N-t-butyloxycarbonylpiperidinyl)ethyl]-3-oxo (12-3)

Treatment of 1-10 (1.0 g, 2.7 mmoles) with 12-2 (0.524 g, 4.0 mmoles), N methylmorpholine (4.0 mmoles) and BOP (1.78 g, 4.0 mmoles) in CH$_3$CN (15 ml) as described for 6-3 provided crude 12-3. This was purified by flash chromatography on silica gel eluting with EtOAc (9)/Hexane (1) to give pure 12-3 as a white solid.

$^1$H NMR (300 MHz, CDCl$_3$) δ 1.20 (2H, m), 1.33 (6H, s), 1.48 (9H, s), 1.80 (2H, bd), 2.71 (2H, bt), 3.64 (2H, d), 3.73 (2H, t), 3.77 (3H, s), 4.13 (2H, m), 4.44 (2H, s), 6.94 (1H, t), 7.57 (1H, d), 8.11 (1H, d), 8.13 (1H, s).

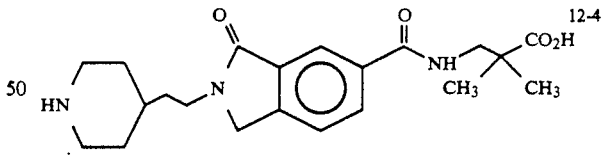

12-4

1-H-Isoindole-5-carboxamide, 2,3-dihydro-N-[(2-carboxy-2-methyl)propyl]-2-[2-(4-piperidinyl)ethyl]-3-oxo (12-4)

12-3 (0.5 g, 1.0 mmoles) was treated with LiOH.H$_2$O (0.216 g, 5.0 mmoles) as described for 6-2 to give the desired acid as a white solid.

$^1$H NMR (300 MHz, CD$_3$OD) δ 1.13 (2H, m), 1.25 (6H, s), 1.45 (9H, s), 1.65 (2H, m), 1.80 (2H, bd), 2.72 (2H, m), 3.68 (2H, m0, 3.70 (2H, t), 4.05 (2H, bd), 4.56 (2H, s), 7.67 (1H, d), 8.04 (1H, dd), 8.15 (s).

This acid (0.40 g) was dissolved in EtOAc and was treated with HCl gas as described for 6-4 to give pure 12-4 as a white solid.

$^1$H NMR (300 MHz, D$_2$O) δ 1.14 (6H, s), 1.35 (2H, m), 1.49 (1H, m), 1.60 (2H, q), 1.90 (2H, bd), 2.81 (2H, t), 3.30 (2H, bd), 3.47 (2H, s), 3.57 (2H,. t), 4.48 (2H, s), 7.55 (1H, d), 7.82 (1H, d), 7.90 (1H, s).

SCHEME 13

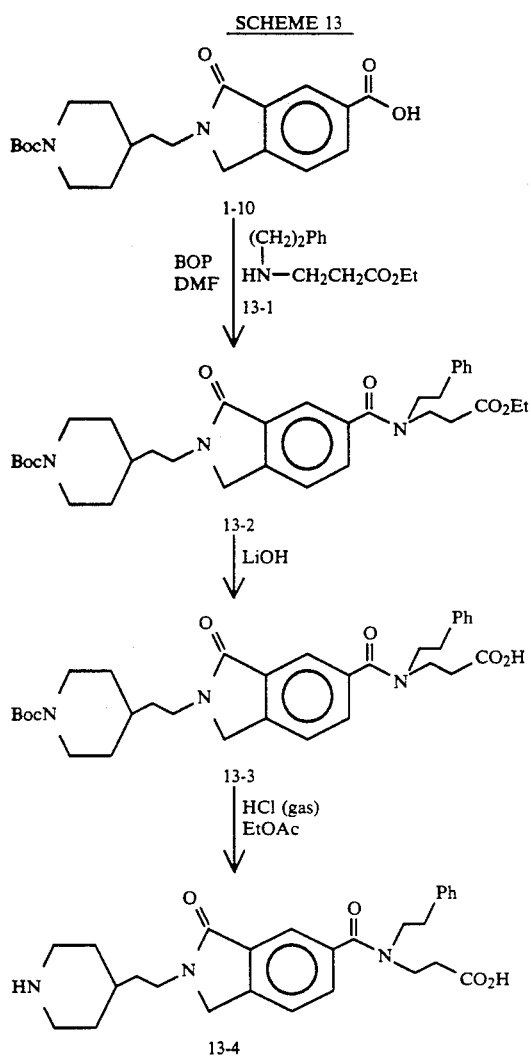

1H-Isoindole-5-carboxamide, 2,3-dihydro-N-[N-phenethyl-N-2-carboethoxyethyl]-2-[2-(4-N-t-butyloxycarbonylpiperidinyl)ethyl]-3-oxo (13-2)

1-10 (0.388 g, 1.0 mmoles) was treated with ethyl 3-(N-phenethyl)aminopropionate (0.22 g, 1.0 mmoles) (prepared by treatment of phenethylamine with ethyl acrylate), triethylamine (0.243 g, 2.4 mmoles) and BOP (0.53 g, 1.2 mmoles) in DMF (15 ml) and the resulting solution was stirred at room temperature for 18 hours. The solvent was then removed and the residue was diluted with H₂O (100 ml) and extracted with EtOAc (3×100 ml portions). The organic phase was washed with 10% KHSO₄ solution, brine, saturated NaHCO₃ solution, brine and dried (Na₂SO₄) Solvent removal gave 13-2 as an oil.

¹H NMR (300 MHz, CDCl₃) δ 1.07–1.35 (6H, m), 1.48 (9H, s), 1.62 (3H, m), 1.75 (2H, bd), 2.72 (4H, m), 3.00 (1H, m), 3.50 (2H, m), 3.67 (2H, t), 3.83 (2H, m), 4.10 (5H, m), 4.38 (2H, s), 6.94 (1H, bs), 7.30 (6H, m), 7.50 (1H, m), 7.67 (1H, m).

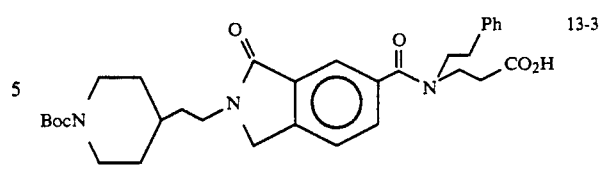

1-H-Isoindole-5-carboxamide, 2,3-dihydro-N-[N-phenethyl-N-(2-carboxyethyl)]-2-[2-(4-N-t-butyloxycarbonylpiperidinyl)ethyl]-3-oxo (13-3)

13-2 (0.60 g, 1.0 mmoles) was treated with LiOH.H₂O (0.127 g, 3.0 mmoles) as described for 6-2 to give 13-3 as a white solid. R$_f$ 0.45 (silica gel, CHCl₃ (9)/MeOH (5)/HOAc (1)).

¹H NMR (300 MHz, CDCl₃) δ 1.17 (2H, m), 1.47 (9H, s), 1.63 (3H, m), 1.75 (2H, bd), 2.67 (2H, t), 2.80 (3H, m), 3.42 (1H, m), 3.57 (1H, m), 3.67 (2H, t), 3.80 (2H, m), 4.08 (3H, m), 4.37 (2H, s), 6.93 (1H, m), 7.25 (6H, m), 7.48 (1H, m), 7.70 (1H, m).

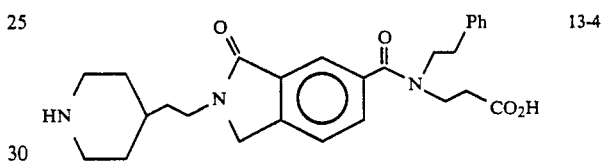

1-H-Isoindole-5-carboxamide, 2,3-dihydro-N-[N-phenethyl-N-(2-carboxyethyl)]-2-[2-(4-piperidinyl)ethyl]-3-oxo (13-4)

13-3 was treated with HCl (gas) in EtOAc as described for 6-4 to give pure 13-4 as a white solid. R$_f$0.25 (silica gel, EtOH (10)/H₂O (1)/NH₄OH (1)).

¹H NMR (300 MHz, CD₃OD) δ 1.45 (2H, m), 1.62 (2H, m), 1.71 (2H, m), 2.07 (2H, bd), 2.45 (1H, m), 2.78 (2H, m), 2.95 (3H, m), 3.37 (3H, bd), 3.57 (1H, bt), 3.72 (2H, t), 3.83 (2H, m), 3.55 (2H, s), 6.95 (1H, m), 7.20 (4H, bs), 7.33 (1H, bs), 7.45 (1H, bs), 7.55 (1H, m), 7.66 (1H, m)

SCHEME 14

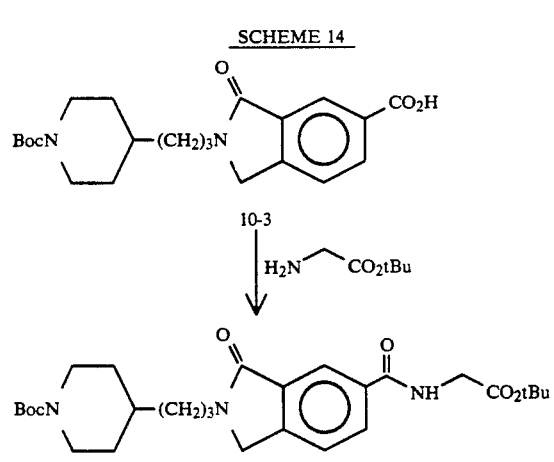

-continued
SCHEME 14

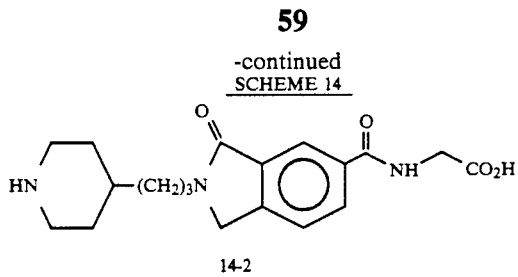

14-2 b 1-H-Isoindole-5-carboxamide, 2,3-dihydro N-[t-butyloxycarbonylmethyl]-2-[3-(4-N-t-butyloxycarbonylpiperidinyl)propyl]-3oxo (14-1)

Treatment of 10-3 with glycine t-butyl ester as described for 6-3 gave 14-1.

$^1$H NMR (300 MHz, CDCl$_3$) δ 1.13 (2H, m), 1.30 (2H, m), 1.41 (9H, s), 1.52 (9H, s), 1.73 (4H, m), 2.69 (2H, t), 3.65 (2H, t), 4.10 (2H, bd), 4.16 (2H, d), 4.45 (2H, s), 7.53 (1H, d), 8.10 (1H, d), 8.22 (1H, s).

1-H-Isoindole-5-carboxamide, 2,3, dihydro N-[carboxymethyl]-2-[3-(4-piperidinyl)propyl]-3-oxo (14-2)

Treatment of 14-1 with HCl gas in EtOAc as described for 6-4 gave 14-2 as a white solid. 1H NMR (300 MHz, CD$_3$OD) δ 1.30 (4H, m), 1.65 (4H, m), 1.90 (2H, bd), 2.59 (2H, t), 2.90 (2H, t), 3.30 (2H, bd), 3.58 (4H, m), 4.50 (2H, s), 7.58 (1H, d), 7.98 (1H, d), 8.07 (1H, s).

$^1$H NMR (300 MHz, CD$_3$OD)δ 1.61 (2H, m), 1.75 (2H, m), 2.90 (2H, t), 3.24 (1H, m), 3.63 (2H, t), 3.85 (3H, s), 4.53 (2H, s), 7.62 (1H, d), 8.18 (1H, d) 8.28 (1H, s)

1-H-Isoindole-5-carboxylic acid-2,3-dihydro N-[2-(4-N-t-butyloxycarbonyamino)butyl]-3-oxo (15-2)

15-1 (1.11 g, 4.24 mmoles) was treated with Boc$_2$O (1.17 g, 5.36 mmoles) as described for 3-1 Crude residue was purified by flash chromatography on silica gel eluting with 30% acetone/hexane to give the desired protected ester as an oil. R$_f$0.7 silica gel, 30% acetone/hexane.

This ester (0.85 g, 2.34 mmoles) was dissolved in THF(1)/CH$_3$OH(1)/H$_2$O(1) (30 ml) and treated with LiOH.H$_2$O (0.52 g, 12.4 mmoles) as described for 3-2 to give 15-2 as a white solid.

$^1$H NMR (300 MHz, CD$_3$OD) δ 1.36 (9H, s), 1.44 (2H, m), 1.66 (4H, m), 3.01 (2H, t), 3.60 (2H, t), 4.54 (2H, s), 7.62 (1H, d), 8.20 (1H, d), 8.35 (1H, s).

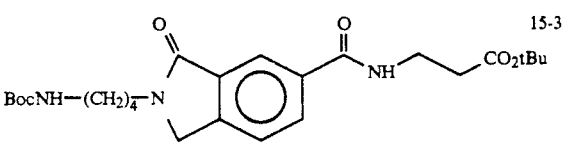

15-3

1-H Isoindole-5-carboxamide, 2,3-dihydro-N-[2-(t-butyloxycarbonyl)ethyl]-2-[4-(N-t-butyloxycarbonyl)-

SCHEME 15

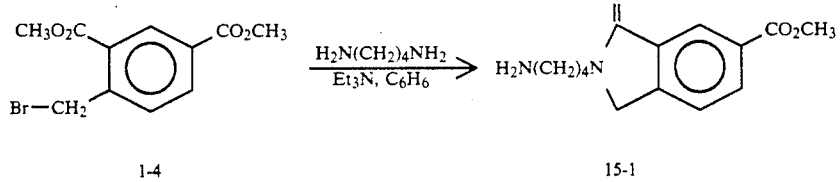

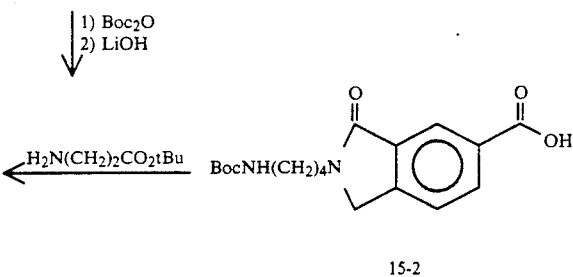

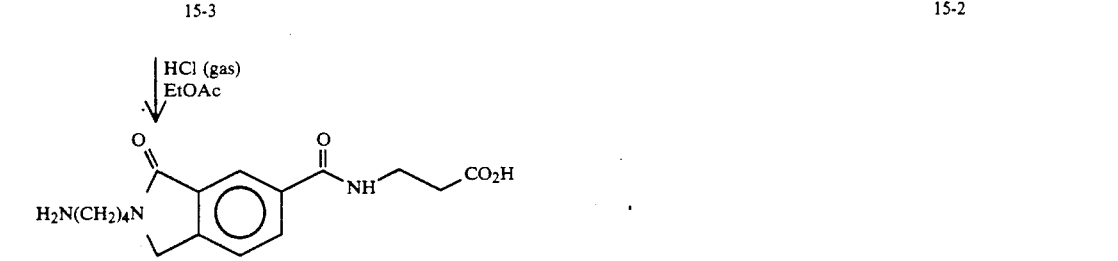

15-4

Methyl-1H-Isoindole-5-carboxylate, 2,3-dihydro-N-[2-(4-aminobutyl)]-3-oxo (15-1)

1-4(2.56 g, 8.92 mmoles)was treated with 1,4 diaminobutane (10.9 mmoles) as described for 1-9 to give crude 15-1. This was purified by flash chromatography on silica gel eluting with 25% CH$_3$OH/CHCl$_3$ (NH$_3$) to give pure 15-1 as a solid.

butyl]-3-oxo(15-3)

Treatment of 15-2 (0.75 g, 2.07 mmoles) in CH$_3$CN (12 ml) with β-alanine t-butyl ester (0.39 g, 2.54 mmoles), Et$_3$N (14.3 mmoles) and BOP (1.40 g, 3.16 mmoles) as described for 3-3 gave crude 15-3. This was purified by flash chromatography on silica gel eluting with 75% EtOAc/hexane to give pure 15-3 as a white solid. $R_f$ 0.25 (silica gel, 75% EtOAc/hexanes).

$^1$H NMR (300 MHz, CDCl$_3$) δ 1.42 (9H, s), 1.44 (9H, s), 1.52 (2H, m), 1.77 (2H, m), 2.55 (2H, t), 3.19 (2H, m), 3.67 (4H, m), 4.43 (2H, s), 7.00 (1H, bt), 7.52 (1H, d), 8.09 (1H, d), 8.10 (1H, s).

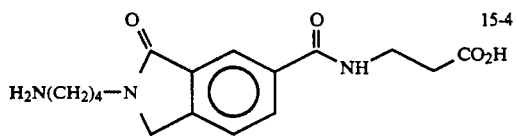

1-H-Isoindole-5-carboxamide, 2,3-dihydro N-[2-carboxyethyl]-2-[4-aminobutyl]-3-oxo(15-4)

Treatment of 15-3 (0.51 g, 1.07 mmoles) in EtOAc with HCl gas as described for 3-4 provided pure 15-4 as a white solid.

$^1$H NMR (300 MHz, D$_2$O), δ 1.63 (4H, m), 2.64 (2H, t), 2.92 (2H, t), 3.52 (4H, m), 4.46 (2H, s), 7.55 (1H, d), 7.81 (1H, d), 7.85 (1H, s).

reaction mixture was then stirred at room temperature for 16 hrs.

The solvent was then removed and the residue was dissolved in EtOAc and 10% aqueous KHSO$_4$ solution. The aqueous phase was separated, washed with EtOAc and made basic to pH 12. This was extracted with EtOAc, and the extracts were combined, washed with brine, and dried (Na$_2$SO$_4$). Solvent removal provided 16-2.

$^1$H NMR (300 MHz, CD$_3$OD) δ 1.24 (2H, m), 1.46 (3H, t), 1.43 (9H, s), 1.66 (2H, q), 1.80 (2H, bd), 3.67 (4H, m), 4.10 (2H, bd), 4.17 (2H, q), 4.57 (2H, s), 7.04 (1H, d), 7.67 (1H, m), 8.06 (1H, m), 8.17 (1H, d).

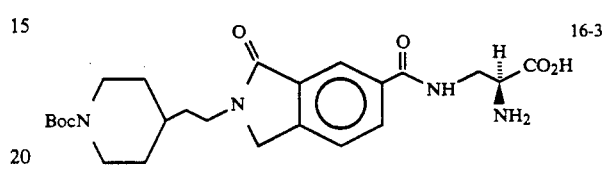

SCHEME 16

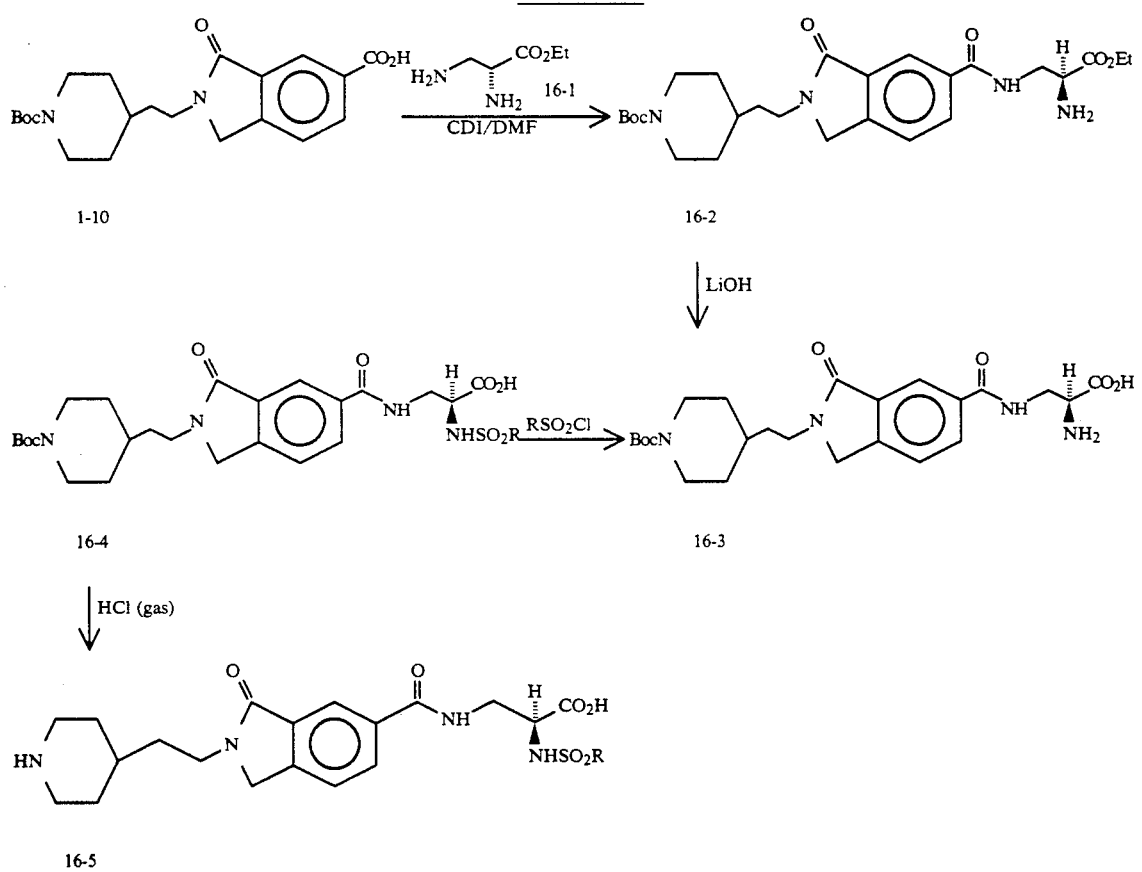

1-H-Isoindole-5-carboxamide, 2,3-dihydro-N-[ethyl-3-(2(S) aminopropionate)]-2-[2-(4-N-t-butyloxycarbonylpiperidinyl]-3-oxo (16-2)

A solution of 1-10 (1.5 g, 3.87 mmoles) in DMF (15 ml) at room temperature was treated with carbonyl diimidazole (0.627 g, 3.87 mmoles) (CDI) and after 2 hours this solution was added dropwise to a DMF solution of ethyl 2(S),3-diaminopropionate (1.5 g, 7.74 mmoles) and N-methylmorpholine (23.2 mmoles). The 1-H-Isoindole-5-carboxamide, 2,3-dihydro-N-[3-[2(S)aminopropanoic acid]-2-[2-(4-N-t-butyloxycarbonylpiperidinyl]-3-oxo (16-3)

Treatment of 16-2 (0.6 g, 1.2 mmoles) with LiOH.H$_2$O (0.25 g, 6.0 mmoles) as described for 1-10 gave 16-3.

$^1$H NMR (300 MHz, D$_2$O) δ 0.92 (2H, m), 1.27 (9H, s), 1.46 (4H, m), 2.58 (2H, 6), 3.48 (4H, m), 3.83 (2H, bd), 4.38 (2H, s), 6.96 (1H, s), 7.50 (1H, d), 7.82 (1H, d), 7.87 (1H, s).

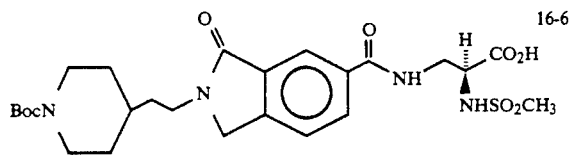

16-6

1-H-Isoindole-5-carboxamide, 2,3-dihydro-N-[3-[2(S)-methylsulfonylamino)propanoic acid)]-2-[2-(4-N-t-butyloxycarbonylpiperidinyl]-3-oxo (16-6)

A solution of 16-6 (0.55 g, 1.2 mmoles) in $H_2O$ (15 ml)/dioxane (3 ml) was cooled to 0°–10° and treated with 1N NaOH soln. (1.5 ml) and methane sulfonyl chloride (2.4 mmoles) in 3 ml dioxane was added dropwise while also adding 1N NaOH solution to keep the pH at 10–12. This cycle of $CH_3SO_2Cl$ addition at basic pH was carried out 5 times at which Point all 16-6 was consumed. The acidity was carefully adjusted to pH 2–3 with 10% $KHSO_4$ solution and this was extracted with EtOAc (4 portions). The combined organics were washed with brine, dried ($Na_2SO_4$) and the solvent removed. The residue was purified by flash chromatography on silica gel eluting with $CH_2Cl_2$ (9)/MeOH (0.8)/HOAc (0.8) to give 16-6 as a white solid. $R_f$ 0.31.

$^1H$ NMR (300 MHz, $CD_3OD$) δ 1.25 (2H, m), 1.45 (9H, s), 1.65 (2H, q), 1.80 (2H, bd), 2.72 (2H, m), 2.97 (3H, s), 3.70 (3H, m), 3.86 (1H, m), 4.05 (2H, bd), 4.34 (1H, m), 4.56 (2H, s), 7.66 (1H, d), 8.08 (1H, d), 8.19 (1H, s).

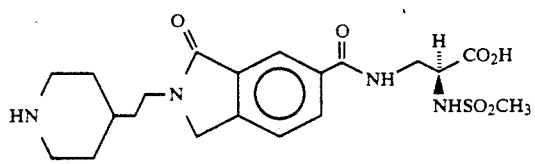

16-7

1-H-Isoindole-5-carboxamide, 2,3-dihydro-N-[3-(2(S)methylsulfonylamino)propionic acid]-2-[2-(4-piperidinyl)ethyl]-3-oxo (16-7)

Treatment of 16-6 (0.22 g, 0.39 mmoles) with HCl gas in EtOAc as described for 1-12 gave 16-7 as a white solid.

$^1H$ NMR (300 MHz, $D_2O$) δ 1.35 (2H, m), 1.59 (2H, m), 1.87 (2H, bd), 2.78 (2H, bt), 2.95 (3H, m), 3.27 (2H, bd), 3.55 (3H, m), 3.78 (1H, m), 4.20 (1H, m), 4.48 (2H, s), 7.56 (1H, m), 7.87 (1H, m), 7.95 (1H, bs).

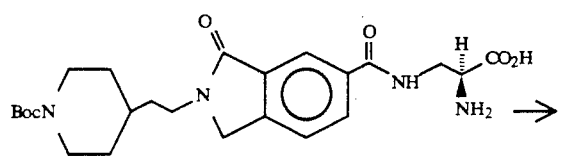

16-3

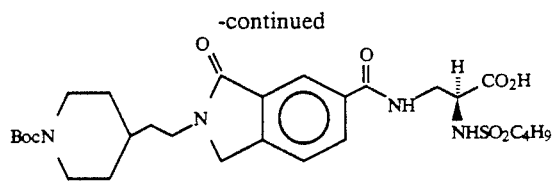

16-8

↓ HCl gas
EtOAc

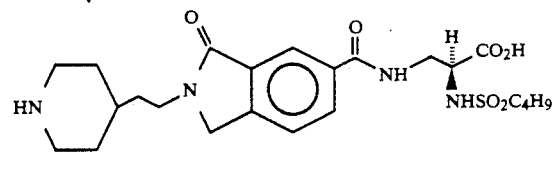

16-9

1-H Isoindole-5-carboxamide, 2,3-dihydro-N-[3-(2(S)-n-butylsulfonylamino)propanoic acid]-2-[2-(4-N-t-butyloxycarbonylpiperidinyl)]-3-oxo (16-8)

Treatment of 16-3 (0.836 mmoles) with n-butylsulfonyl chloride (1.67 mmoles) as described for 16-6 gave 16-8 as a white solid.

$^1H$ NMR (300 MHz, $CD_3OD$) δ 0.85 (6H, m), 1.13 (2H, m), 1.35 (4H, m), 1.45 (9H, s), 1.65 (2H, m), 1.75 (2H, m), 2.70 (2H, m), 3.04 (2H, t), 3.68 (2H, m), 3.83 (1H, m), 4.04 (2H, bd), 4.53 (2H, s), 7.62 (1H, d), 8.05 (1H, d), 8.18 (1H, s).

$^1$-H-Isoindole-5-carboxamide, 2,3-dihydro-N [3-(2(S)-n-butylsulfonylamino)propionic acid]-2-[2-(4-piperidinyl)ethyl[-3-oxo (16-9)

Treatment of 7-8 in EtOAc with HCl gas as described for 1-12 gave pure 16-9 as a white solid.

$^1H$ NMR (300 MHz, $CD_3OD$) δ 0.59 (2H, t), 1.12 (2H, m), 1.35 (2H, m), 1.50 (2H, m), 1.59 (2H, m), 1.90 (2H, bd), 2.80 (2H, t), 2.98 (2H, t), 3.29 (2H, bd), 3.42 (1H, m), 3.60 (2H, t), 3.70 (1H, m), 4.50 (2H, s), 7.59 (1H, d), 7.91 (1H, d), 7.98 (1H, s).

What is claimed is:

1. A fibrinogen receptor antagonist of the following formula:

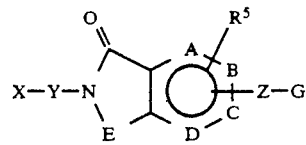

I wherein G is

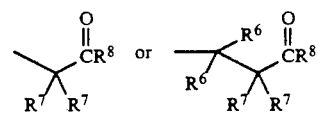

wherein:

A, B, C, D and E represent a carbon atom;
$R^1$, $R^2$, $R^3$ and $R^4$ are independently selected from the group consisting of hydrogen, $C_{1-10}$ alkyl, phenyl $C_{0-8}$ alkyl, oxo, thio, amino $C_{0-8}$ alkyl, $C_{1-3}$ acylamino $C_{0-8}$ alkyl, $C_{1-6}$ alkylamino $C_{0-8}$ alkyl, $C_{1-6}$ dialkylamino $C_{0-8}$ alkyl, $C_{1-4}$ alkoxy $C_{0-6}$ alkyl, carboxy $C_{0-6}$ alkyl, $C_{1-3}$ alkoxycarbonyl $C_{0-6}$ alkyl, carboxy $C_{0-6}$ alkyloxy and hydroxy $C_{0-6}$ alkyl;

Y is $C_{0-8}$ alkyl, $C_{0-8}$ alkyl-$NR^3$—CO—$C_{0-8}$ alkyl, $C_{0-8}$ alkyl-$CONR^3$—$C_{0-8}$ alkyl, $C_{0-8}$ alkly-O—$C_{0-8}$ alkyl, $C_{0-8}$ alkyl-$S(O_n)$—$C_{0-8}$ alkyl, or $C_{0-8}$ alkyl-$SO_2$—$NR^3C_{0-8}$ alkyl-, $C_{0-8}$ alkyl-$NR^3$—$SO_2$—$C_{0-8}$ alkyl-, $C_{1-8}$ alkyl-CO—$C_{0-8}$ alkyl;

Z is

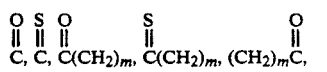

O, S, SO, $SO_2$, $SO_2(CH_2)_m$, $(CH_2)_mSO_2$,

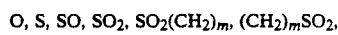

$CNR^3$, $NR^3C$, $NR^3SO_2$ or $CR^3=CR^4$, wherein m is 0–6;

$R^5$ is hydrogen $C_{1-6}$ alkyl, $C_{0-6}$ alkylcarboxy $C_{0-6}$ alkyl, $C_{0-6}$ alkyloxy $C_{0-6}$ alkyl, hydroxy $C_{0-6}$ alkyl, or halogen;

$R^6$ is hydrogen, $C_{1-8}$ alkyl, phenyl $C_{0-6}$ alkyl, $C_{3-8}$ cycloalkyl $C_{0-6}$ alkyl, $C_{0-6}$ alkylcarboxy $C_{0-6}$ alkyl, carboxy $C_{0-6}$ alkyl, $C_{1-4}$ alkyloxy $C_{0-6}$ alkyl, hydroxy $C_{0-6}$ alkyl, provided that any of which groups may be substituted or unsubstituted independently with $R^1$ or $R^2$, and provided that, when two $R^6$ groups are attached to the same carbon, they may be the same or different;

$R^7$ is hydrogen fluorine $C_{1-8}$ alkyl, $C_{3-8}$ cycloalkyl, phenyl $C_{0-6}$ alkyl, $C_{0-6}$ alkylamino $C_{0-6}$ alkyl, $C_{0-6}$ dialkylamino $C_{0-6}$ alkyl, $C_{1-8}$ alkylsulfonylamino $C_{0-6}$ alkyl, phenyl $C_{0-6}$ alkylsulfonylamino $C_{0-6}$ alkyl, $C_{1-8}$ alkyloxycarbonylamino $C_{0-8}$ alkyl, phenyl $C_{0-8}$ alkyloxycarbonylamino $C_{0-8}$ alkyl, $C_{1-8}$ alkylcarbonylamino $C_{0-6}$ alkyl, phenyl $C_{0-6}$ alkylcarbonylamino $C_{0-6}$ alkyl, $C_{0-8}$ alkylaminocarbonylamino $C_{0-6}$ alkyl, phenyl $C_{0-8}$ alkylaminocarbonylamino $C_{0-6}$ alkyl, $C_{1-6}$ alkylsulfonyl $C_{0-6}$ alkyl, phenyl $C_{0-6}$ alkylsulfonyl $C_{0-6}$ alkyl, $C_{1-6}$ alkylcarbonyl $C_{0-6}$ alkyl phenyl $C_{0-6}$ alkylcarbonyl $C_{0-6}$ alkyl, $C_{1-6}$ alkylthiocarbonylamino $C_{0-6}$ alkyl phenyl $C_{0-6}$ alkylthiocarbonylamino $C_{0-6}$ alkyl wherein groups may be unsubstituted or substituted with one or more substituents selected from $R^1$ and $R^2$, and provided that when two $R^7$ groups are attached to the same carbon atom, they may be the same or different;

$R^8$ is hydroxy, ethyl, t-butyl, $C_{1-8}$ alkyloxy, phenyl $C_{0-6}$ alkyloxy, aryl $C_{1-8}$ alkylcarbonyloxy $C_{1-4}$ alkyloxy, or proline joined by an amide linkage and wherein the carboxylic acid moiety of proline is as the free acid or is esterified by $C_{1-6}$ alkyl.

2. A compound of claim 1, having the formula:

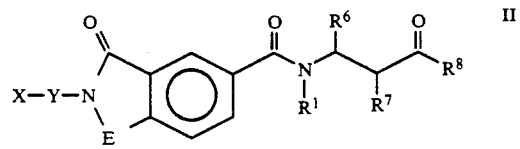

wherein:

E is carbon;

X is piperidine;

$R^1$ and $R^2$ are independently chosen from: hydrogen, $C_{1-6}$ alkyl, phenyl $C_{0-6}$ alkyl carboxy $C_{0-6}$ alkyl, hydroxy $C_{0-6}$ alkyl, $C_{1-3}$ alkyloxy $C_{0-6}$ alkyl, or amino $C_{0-6}$ alkyl;

Y is $C_{0-6}$ alkyl, $C_{1-6}$ alkyl-CO—$C_{0-6}$ alkyl, or $C_{0-6}$ alkyl-$NR^3$—CO-$C_{0-6}$ alkyl;

$R^6$ and $R^7$ are as previously defined in claim 1, and $R^8$ is hydroxy, ethyl, t-butyl, $C_{1-6}$ alkyloxy, phenyl $C_{1-4}$ alkyloxy, or $C_{1-6}$ alkylcarbonyloxy $C_{1-4}$ alkyloxy.

3. A compound of claim 1 selected from the group of

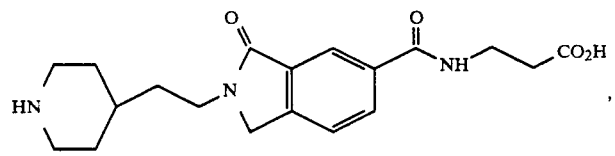

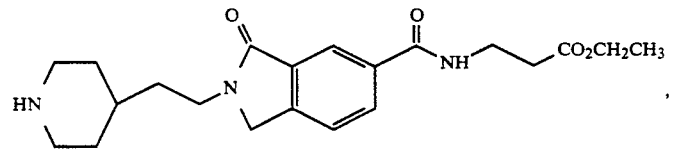

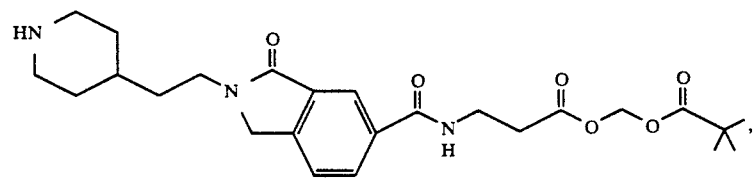

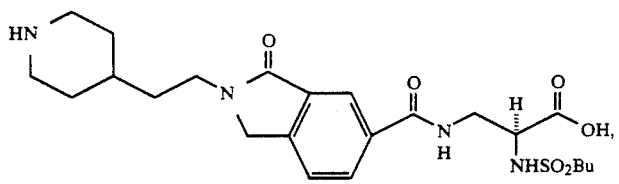
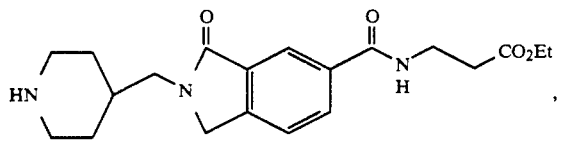
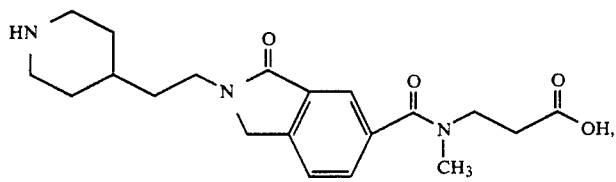
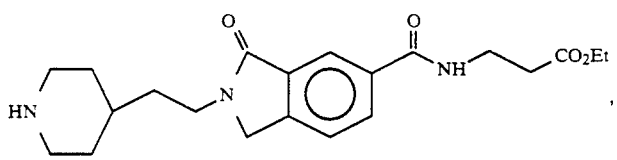
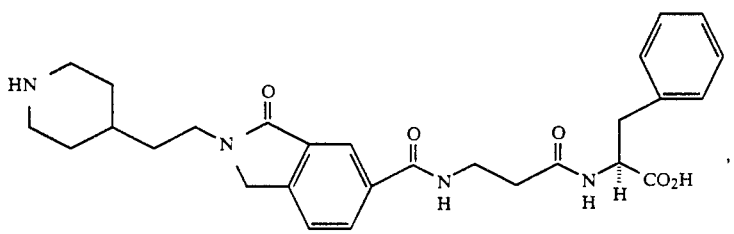
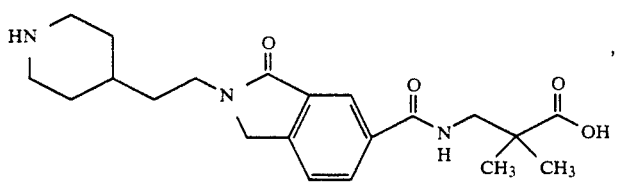
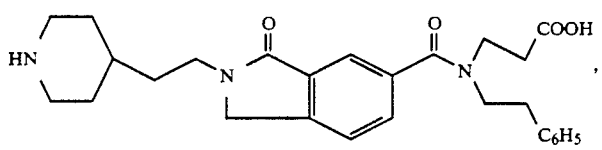
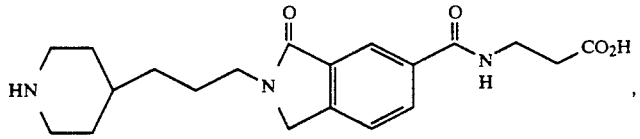
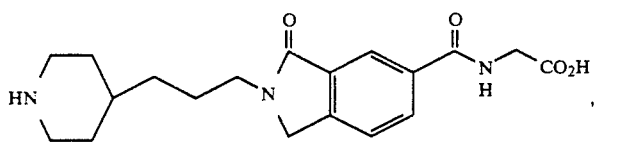

-continued

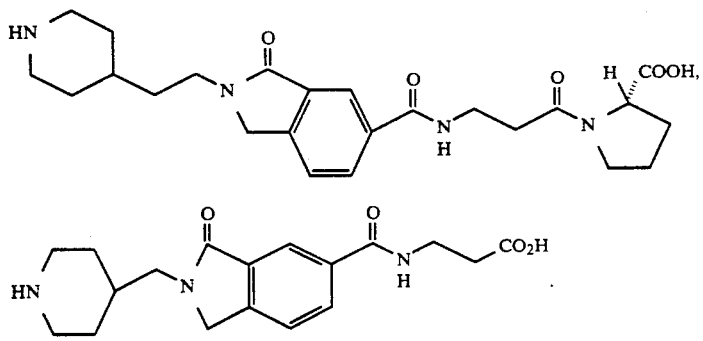

4. A composition for inhibiting the binding of fibrinogen to blood platelets in a mammal, comprising a compound of claim 1 and a pharmaceutically acceptable carrier.

5. A composition for inhibiting the aggregation of blood platelets in a mammal, comprising a compound of claim 1 and a pharmaceutically acceptable carrier.

6. A method for inhibiting the binding of fibrinogen to block platelets in a mammal, comprising administering to the mammal a composition of claim 5.

7. A method for inhibiting the aggregation of blood platelets in a mammal, comprising administering to the mammal the composition of claim 5.